United States Patent
Kaufmann et al.

(10) Patent No.: US 11,167,137 B2
(45) Date of Patent: Nov. 9, 2021

(54) MODULAR IMPLANT DELIVERY AND POSITIONING SYSTEM

(71) Applicant: IotaMotion, Inc., Iowa City, IA (US)

(72) Inventors: Christopher Kaufmann, Iowa City, IA (US); Adam Hahn, Pittsburgh, PA (US); Allan Henslee, Houston, TX (US); Marlan Hansen, Solon, IA (US); Eric Timko, Wayzata, MN (US)

(73) Assignee: IotaMotion, Inc., Iowa City, IA (US)

( * ) Notice: Subject to any disclaimer, the term of this patent is extended or adjusted under 35 U.S.C. 154(b) by 0 days.

(21) Appl. No.: 17/196,723

(22) Filed: Mar. 9, 2021

(65) Prior Publication Data
US 2021/0187295 A1    Jun. 24, 2021

Related U.S. Application Data

(63) Continuation of application No. 16/486,030, filed as application No. PCT/US2018/018182 on Feb. 14, (Continued)

(51) Int. Cl.
*A61N 1/36* (2006.01)
*A61B 34/30* (2016.01)
(Continued)

(52) U.S. Cl.
CPC ...... *A61N 1/36039* (2017.08); *A61B 17/3468* (2013.01); *A61B 34/30* (2016.02);
(Continued)

(58) Field of Classification Search
CPC ............ A61N 1/36038; A61N 1/36039; A61N 1/0541; A61N 1/372; A61B 17/3468;
(Continued)

(56) References Cited

U.S. PATENT DOCUMENTS 3,610,877 A * 10/1971 Driscoll ............... B23K 35/222
                                                          219/145.21
4,383,532 A     5/1983 Dickhudt
(Continued)

FOREIGN PATENT DOCUMENTS

AU    2016323477 A1    4/2018
CA     2997735 A1    3/2017
(Continued)

OTHER PUBLICATIONS

"U.S. Appl. No. 15/759,643, Final Office Action dated Mar. 29, 2021", 13 pgs.
(Continued)

*Primary Examiner* — Phong Son H Dang
(74) *Attorney, Agent, or Firm* — Schwegman Lundberg & Woessner, P.A.

(57) ABSTRACT

This document discusses, among other things, systems and methods for robotically assisted implantation of an implant in a patient. A system includes an external positioning unit configured to engage an elongate member of the implant, and a control console communicatively coupled to the external positioning unit. The control console may have a user interface that enables a user to input motion control instructions. The control console may generate a motion control signal, according to a specific motion control instruction, to control the external positioning unit to propel the implant into a target implant site. The system may be used to robotically control the delivery and positing of a cochlear implant during a hearing-preservation cochlear implant surgery.

30 Claims, 16 Drawing Sheets

Related U.S. Application Data 2018, now Pat. No. 10,987,513, and a continuation of application No. 15/759,643, filed as application No. PCT/US2016/039342 on Jun. 24, 2016.

(60) Provisional application No. 62/573,487, filed on Oct. 17, 2017, provisional application No. 62/458,846, filed on Feb. 14, 2017, provisional application No. 62/218,359, filed on Sep. 14, 2015.

(51) Int. Cl.

| | | |
|---|---|---|
| A61B 17/34 | (2006.01) | |
| A61N 1/05 | (2006.01) | |
| A61B 34/20 | (2016.01) | |
| A61B 17/00 | (2006.01) | |

(52) U.S. Cl.
CPC .. *A61N 1/0541* (2013.01); *A61B 2017/00039* (2013.01); *A61B 2017/00973* (2013.01); *A61B 2034/2051* (2016.02)

(58) Field of Classification Search
CPC .......... A61B 34/30; A61B 2017/00039; A61B 2034/2051; A61B 2017/00973; A61B 2017/00477; A61B 2017/00398
See application file for complete search history.

(56) References Cited

U.S. PATENT DOCUMENTS

| | | | |
|---|---|---|---|
| 4,532,930 | A | 8/1985 | Crosby et al. |
| 4,637,404 | A | 1/1987 | Gessman |
| 5,201,765 | A | 4/1993 | Netterville et al. |
| 5,306,298 | A | 4/1994 | Godley, III et al. |
| 5,593,439 | A | 1/1997 | Cummings et al. |
| 5,758,396 | A | 6/1998 | Jeon et al. |
| 7,524,320 | B2 | 4/2009 | Tierney et al. |
| 7,691,098 | B2 | 4/2010 | Wallace et al. |
| 8,010,210 | B2 | 8/2011 | Rau |
| 8,229,574 | B2 | 7/2012 | Parker et al. |
| 8,583,261 | B2 | 11/2013 | Llinas et al. |
| 8,594,799 | B2 | 11/2013 | Haller et al. |
| 8,886,331 | B2 | 11/2014 | Labadie et al. |
| 9,675,446 | B2 | 6/2017 | Jaber et al. |
| 9,700,408 | B1 | 7/2017 | Sataloff |
| 9,986,998 | B2 | 6/2018 | Martin et al. |
| 10,085,806 | B2 | 10/2018 | Hagn et al. |
| 2003/0171758 | A1 | 9/2003 | Gibson et al. |
| 2004/0236390 | A1 | 11/2004 | Dadd et al. |
| 2005/0004627 | A1 | 1/2005 | Gibson et al. |
| 2005/0245991 | A1 | 11/2005 | Faltys et al. |
| 2006/0241723 | A1 | 10/2006 | Dadd et al. |
| 2007/0156123 | A1 | 7/2007 | Moll et al. |
| 2007/0225787 | A1 | 9/2007 | Simaan et al. |
| 2008/0077221 | A1 | 3/2008 | Milojevic et al. |
| 2008/0188931 | A1 | 8/2008 | Kwon |
| 2010/0114288 | A1 | 5/2010 | Haller et al. |
| 2010/0145138 | A1 | 6/2010 | Forsell |
| 2010/0145143 | A1 | 6/2010 | Salomon et al. |
| 2011/0106101 | A1 | 5/2011 | Tortonese |
| 2011/0208031 | A1 | 8/2011 | Wolfe et al. |
| 2011/0264038 | A1 | 10/2011 | Fujimoto et al. |
| 2012/0041531 | A1 | 2/2012 | Dadd et al. |
| 2012/0071890 | A1 | 3/2012 | Taylor et al. |
| 2012/0150293 | A1 | 6/2012 | Hoffman et al. |
| 2013/0138117 | A1 | 5/2013 | Abbott et al. |
| 2013/0172901 | A1 | 7/2013 | Bozorg et al. |
| 2013/0245569 | A1 | 9/2013 | Jolly et al. |
| 2013/0296884 | A1 | 11/2013 | Taylor et al. |
| 2013/0331779 | A1 | 12/2013 | Dhanasingh et al. |
| 2014/0222207 | A1 | 8/2014 | Bowling et al. |
| 2014/0276391 | A1 | 9/2014 | Alan |
| 2014/0350640 | A1 | 11/2014 | Patrick et al. |
| 2014/0358174 | A1 | 12/2014 | Thenuwara et al. |
| 2015/0032123 | A1 | 1/2015 | Jolly et al. |
| 2015/0032124 | A1 | 1/2015 | Lenarz et al. |
| 2015/0105795 | A1 | 4/2015 | Lenarz et al. |
| 2015/0342445 | A1 | 12/2015 | Jones et al. |
| 2016/0038733 | A1 | 2/2016 | Robinson et al. |
| 2016/0056493 | A1* | 2/2016 | Umeda ................... B05C 19/04 118/114 |
| 2018/0021568 | A1 | 1/2018 | Schachtele et al. |
| 2018/0242967 | A1 | 8/2018 | Meade |
| 2019/0029668 | A1 | 1/2019 | Meade et al. |
| 2019/0142247 | A1 | 5/2019 | Maeda et al. |
| 2019/0282803 | A1 | 9/2019 | Hansen et al. |
| 2020/0038106 | A1 | 2/2020 | Pieper et al. |
| 2020/0046978 | A1 | 2/2020 | Kaufmann et al. |
| 2020/0069386 | A1 | 3/2020 | Betsugi et al. |
| 2020/0329950 | A1 | 10/2020 | Shear et al. |
| 2020/0337725 | A1 | 10/2020 | Kaufmann et al. |

FOREIGN PATENT DOCUMENTS

| | | |
|---|---|---|
| CN | 110430918 A | 11/2019 |
| CN | 112074254 A | 12/2020 |
| EP | 2113283 A1 | 11/2009 |
| EP | 3334492 A1 | 6/2018 |
| EP | 3334492 B1 | 6/2019 |
| EP | 3662971 A1 | 6/2020 |
| WO | WO-2017048342 A1 | 3/2017 |
| WO | WO-2017177208 A1 | 10/2017 |
| WO | WO-2018152203 A2 | 10/2018 |
| WO | WO-2018152203 A3 | 10/2018 |
| WO | WO-2019173107 A1 | 9/2019 |

OTHER PUBLICATIONS

"U.S. Appl. No. 15/759,643, Final Office Action dated Sep. 4, 2020", 15 pgs.

"U.S. Appl. No. 15/759,643, Preliminary Amendment filed Mar. 13, 2018", 12 pgs.

"U.S. Appl. No. 15/759,643, Response filed Dec. 4, 2020 to Non Final Office Action dated Sep. 4, 2020", 9 pgs.

"U.S. Appl. No. 16/486,030, Corrected Notice of Allowability dated Jan. 12, 2021", 7 pgs.

"U.S. Appl. No. 16/486,030, Non Final Office Action dated Sep. 8, 2020", 12 pgs.

"U.S. Appl. No. 16/486,030, Notice of Allowance dated Dec. 24, 2020", 11 pgs.

"U.S. Appl. No. 16/486,030, Preliminary Amendment Filed Aug. 14, 2019", 10 pgs.

"U.S. Appl. No. 16/486,030, Response filed Aug. 10, 2020 to Restriction Requirement dated Jun. 11, 2020", 8 pgs.

"U.S. Appl. No. 16/486,030, Response filed Dec. 8, 2020 to Non Final Office Action dated Sep. 8, 2020", 12 pgs.

"U.S. Appl. No. 16/486,030, Restriction Requirement dated Jun. 11, 2020", 7 pgs.

"U.S. Appl. No. 16/486,030, Supplemental Preliminary Amendment filed", 8 pgs.

"U.S. Appl. No. 16/926,335, Notice of Allowance dated Nov. 9, 2020", 14 pgs.

"U.S. Appl. No. 16/926,335, Response filed Oct. 2, 2020 to Restriction Requirement dated Aug. 4, 2020", 9 pgs.

"U.S. Appl. No. 16/926,335, Restriction Requirement dated Aug. 4, 2020".

"U.S. Appl. No. 16/979,427 Preliminary Amendment filed Sep. 9, 2020", 10 pgs.

"Australian Application Serial No. 2016323477, First Examination Report dated Jun. 29, 2020", 3 pgs.

"Australian Application Serial No. 2016323477, Response filed Dec. 10, 2020 to First Examination Report dated Jun. 29, 2020", 19 pgs.

"Australian Application Serial No. 2019231573, First Examination Report dated Feb. 8, 2021", 6 pgs.

"Chinese Application Serial No. 201880011446.0, Voluntary Amendment filed Feb. 28, 2020", w/English claims, 7 pgs.

"European Application Serial No. 16736687.1, Intention to Grant dated Jan. 7, 2019", 48 pgs.

(56) References Cited

OTHER PUBLICATIONS

"European Application Serial No. 18707575.9, Response to Communication Pursuant to Rules 161 and 162 filed Feb. 25, 2020", 23 pgs.
"European Application Serial No. 19173377.3, Extended European Search Report dated Mar. 4, 2020", 4 pgs.
"European Application Serial No. 19173377.3, Response filed Oct. 25, 2020 to Extended European Search Report dated Mar. 4, 2020", 22 pgs.
"International Application Serial No. PCT/US2016/039342, International Preliminary Report on Patentability dated Mar. 29, 2018", 9 pgs.
"International Application Serial No. PCT/US2016/039342, International Search Report dated Oct. 6, 2016", 4 pgs.
"International Application Serial No. PCT/US2016/039342, Written Opinion dated Oct. 6, 2016", 7 pgs.
"International Application Serial No. PCT/US2018/018182, International Preliminary Report on Patentability dated Aug. 29, 2019", 14 pgs.
"International Application Serial No. PCT/US2018/018182, International Search Report dated Sep. 10, 2018", 7 pgs.
"International Application Serial No. PCT/US2018/018182, Invitation to Pay Add'l Fees and Partial Search Report dated May 23, 2018", 15 pgs.
"International Application Serial No. PCT/US2018/018182, Written Opinion dated Sep. 10, 2018", 12 pgs.
"International Application Serial No. PCT/US2019/020130, International Preliminary Report on Patentability dated Sep. 24, 2020", 7 pgs.
"International Application Serial No. PCT/US2019/020130, International Search Report dated Jun. 12, 2019", 7 pgs.
"International Application Serial No. PCT/US2019/020130, Written Opinion dated Jun. 12, 2019", 10 pgs.
Campbell, Luke, et al., "Intraoperative Real-time Cochlear Response Telemetry Predicts Hearing Preservation in Cochlear Implantation", Otology & Neurotology; vol. 37(4), (Apr. 2016), 10 pgs.
Dahm, MC, et al., "The postnatal growth of the temporal bone and its implications for cochlear implantation in children", Acta Otolaryngol Suppl. 505., (1993), 4-39.
Desrosiers, M, et al., "Precise vocal cord medialization using an adjustable laryngeal implant: a preliminary study", Otolaryngol Head Neck Sur, 109(6), (1993), 1014-1019.
Gantz, Bruce J., et al., "Hybrid 10 Clinical Trial", Audiol Neurotol 2009;14(suppl 1):DOI: 10.1159/000206493, (2009), 7 pgs.
Greene, Nathaniel, et al., "Intracochlear pressure transients during cochlear implant electrode insertion", Otol Neurotol. 37(10), (2016), 1541-1548.
Jurawitz, Marie-Charlot, et al., "Hearing Preservation Outcomes with Different Cochlear Implant Electrodes: Nucleus® Hybrid TM-L24 and Nucleus Freedom TM CI422", Audiol Neurotol 2014;19: 293-309; DOI: 10.1159/000360601, (2014), 17 pgs.
Mittmann, Phillipp, et al., "Intracochlear Pressure Changes due to 2 Electrode Types: An Artificial Model Experiment", Otolaryngology—Head and Neck Surgery, vol. 156(4), (Dec. 2016), 712-716.
Montgomery, William, et al., "Montgomery Thyroplasty Implant for vocal fold immobility: phonatory outcomes", Ann Otol Rhinol Laryngol, 109(4), (2000), 393-400.
Mowry, Sarah E., et al., "New Frontiers in Cochlear Implantation: Acoustic Plus Electric Hearing, Hearing Preservation, and More", Otolaryngologic Clinics of North America. vol. 45, Issue 1., (2012), 187-203.
Woodson, Erika A., et al., "The Hybrid Cochlear Implant: A Review", Cochlear Implants and Hearing Preservation. Adv Otorhinolaryngol. Basel, Karger, 2010, vol. 67., (2010), 125-134.
"U.S. Appl. No. 17/180,087, Preliminary Amendment filed Aug. 12, 2021", 7 pgs.
"U.S. Appl. No. 15/759,643, Response filed Jun. 1, 2021 to Final Office Action dated Mar. 29, 2021", 9 pgs.
"U.S. Appl. No. 15/759,643, Advisory Action dated Jun. 8, 2021", 3 pgs.
"Canadian Application Serial No. 2,997,735, Office Action dated Jun. 17, 2021", 4 pgs.

* cited by examiner

MODULAR IMPLANT DELIVERY AND POSITIONING SYSTEM

CLAIM OF PRIORITY

This patent application is a continuation of U.S. patent application Ser. No. 16/486,030, filed Aug. 14, 2019, which application is a U.S. National Stage Filing under 35 U.S.C. 371 from International Application No. PCT/US2018/018182, filed Feb. 14, 2018, and published as WO 2018/152203 on Aug. 23, 2018, which application claims the benefit of priority to U.S. Provisional Patent Application No. 62/458,846, filed Feb. 14, 2017, and U.S. Provisional Patent Application No. 62/573,487, filed Oct. 17, 2017 which are incorporated by reference herein in their entirety. This patent application also is a continuation of U.S. patent application Ser. No. 15/759,643, filed Mar. 13, 2018, which application is a U.S. National Stage Filing under 35 U.S.C. 371 from International Application No. PCT/US2016/039342, filed Jun. 24, 2016, and published as WO 2017/048342 on Mar. 23, 2017, which application claims the benefit of priority to U.S. Provisional Patent Application No. 62/218,359, filed Sep. 14, 2015 which are incorporated by reference herein in their entirety.

TECHNICAL FIELD

This document relates generally to medical systems and more particularly to systems, devices, and methods for robotic control of delivery and positioning of an implant.

BACKGROUND

The cochlea is the auditory portion of the inner ear. It comprises a spiraled, hollow, conical chamber of bone in which sound waves propagate from the base to the apex of the cochlea. The sound waves vibrate the perilymph that moves hair cells in the organ of Corti, converting the vibrations to electrical signals that are sent to the cochlear nerve. The hair cells and nerves in the basal or outer region of the spiraled cochlea are more sensitive to higher frequencies of sound, and are frequently the first part of the cochlea to lose sensitivity. The apical or inner region of the spiraled cochlea is more sensitive to lower frequencies.

Moderate to profound hearing loss affects a large amount of people worldwide, and may have a significant impact on a patient physical and mental health, education, employment, and overall quality of life. Hearing loss may be caused by partial damage to the cochlea. Many patients with various degrees of hearing loss have partial damage to the cochlea in the high-frequency regions (basal cochlea) from common causes such as noise exposure, drugs, genetic mutations or aging, but may retain adequate low-frequency hearing.

Cochlear implants have been used to treat patients with hearing loss. A cochlear implant is a medical device that comprises an external sound processor, a subcutaneously implantable stimulator, and an electrode assembly sized and shaped for cochlear insertion. The sound processor can convert sound signals into electrical signals, and transmit the electrical signals to the implantable stimulator. Based on the physical properties (e.g., frequencies) of the received electrical signals, the stimulator can generate electrical impulses to stimulate specific regions in the cochlea via an array of electrodes on the electrode assembly surgically inserted into the cochlea. The region for stimulation may be determined based on the frequencies of the received electrical signals. For example, higher frequencies may result in stimulation at the outer or basal cochlear region, and lower frequencies may result in stimulation at the inner or apical cochlear region.

For patients who have lost high-frequency hearing and consequently have significant difficulty with word understanding but who have substantial residual, low-frequency hearing function in apical cochlea, a short electrode assembly may be indicated to electrically stimulate the basal or outer cochlea to restore high-frequency hearing. A cochlear implant surgery may be performed by a surgeon to manually insert the electrode assembly into the damaged portion of a patient cochlea (e.g., basal cochlea), while avoiding or minimizing any trauma to the undamaged cochlear regions to preserve the low-frequency hearing function. The cochlear implant may be used together with a hearing aid that acoustically stimulates the undamaged low-frequency sensitive apical cochlea.

Intracochlear trauma can occur from large pressure spikes generated during the insertion of cochlear implant electrodes. Cochlear implant surgery can also involve insertion of a guide sheath or tube near or partially into the cochlea. Insertion of any solid or flexible bodies, tubes, or sheaths into the cochlea could elicit similar fluid and force spikes. These pressures spikes may be of sufficient intensity to cause trauma similar to that of an acoustic blast injury and are one likely source for postoperative loss of residual hearing. Similar to the insertion trauma cause by electrode insertion, the manual insertion of a sheath or other solid body/tube manually into the cochlea may cause intracochlear fluid pressure spikes and result in intrachochlear damage.

SUMMARY

A hearing-preservation cochlear implant surgery involves implanting an electrode assembly into the damaged cochlear region, while avoiding any trauma to the undamaged cochlear region to preserve any normal residual hearing. In current cochlear implant surgery, a surgeon manually inserts an electrode assembly into patient cochlea. However, a complete manual maneuvering of the electrode assembly may cause undesirable outcome in some patients. For example, manual insertion of electrode assembly may lack precision in implant position and motion control, such as the control of insertion rate, distance, or forces applied to the implant for advancing the electrode assembly to the target cochlear region. This may cause damage to fragile cochlear structures such as local trauma to cochlea wall and hair cells, and result in residual hearing loss.

Complete manual maneuvering of the electrode assembly may also be subject to high inter-operator variability among surgeons. The inter-operator variability is demonstrated in dramatic differences in patient outcomes between institutions and surgeons of differing skill levels. Some patients undergoing hearing-preservation cochlear implant surgery may experience additional hearing decline weeks to years after surgery. Such a continual decline in hearing function may be attributed to an inflammatory response to the trauma inflicted during an initial cochlear implant surgery. Some clinical studies show that techniques aimed at reducing electrode-insertion forces during surgery have improved patient hearing preservation outcomes. For at least reasons, the present inventors have recognized that there remains a need to improve patient outcome following a hearing-preservation cochlear implant surgery, particularly systems, apparatus, and methods that enhance surgical precision in implant delivery and positioning, and reduce the risk of perioperative trauma to undamaged cochlea region.

This document discusses, among other things, systems, devices, and methods for robotically assisted implantation of an implant in a patient, such as for delivering and positioning a cochlear implant for treating hearing loss in a hearing-preservation cochlear implant surgery. The systems and devices discussed can also be adapted for robotically controlling insertion of a guide sheath or tube that may be used in conjunction with electrode implantation. The modular system discussed herein includes an external positioning unit reversibly interfacing with and securely engaging an implant such as a cochlear implant having an elongate member, and a computerized control unit for robotically controlling the external positioning unit to regulate the motion of the implant. The computerized control unit may have a user interface that enables a user (e.g., a surgeon) to program various motion control parameters or to select an implantation protocol. The system may include sensors providing feedback on the position or the motion of the implant, or the force or friction applied to the implant during the implantation procedure. The computerized control unit may regulate the motion of the implant based on user input and the sensor feedback. The control systems may also interface with external systems providing electrophysiological measures to enable closed loop feedback on electrode positioning in real-time during implantation.

Example 1 is a system for robotically assisted implantation of an implant in a patient. The system comprises an external positioning unit configured to engage the implant and robotically deliver and position the implant into a target implantation site, and a control console communicatively coupled to the external positioning unit. The control console may include a controller circuit configured to generate a motion control signal, according to a specific motion control instruction, for controlling the external positioning unit to robotically deliver and position the implant into the target implantation site.

In Example 2, the subject matter of Example 1 optionally includes the implant that may include an elongate member. The external positioning unit may include a coupling unit configured to interface with the elongate member of the implant, and to frictionally move the elongate member in response to the motion control signal.

In Example 3, the subject matter of Example 2 optionally includes the implant that may include a cochlear implant having an electrode array disposed on the elongate member.

In Example 4, the subject matter of any one or more of Examples 2-3 optionally includes the coupling unit that may include at least two rollers arranged and configured to: engage, through compression between respective radial outer surfaces of the at least two rollers, at least a portion of the elongate member of the implant; and to rotate to propel the implant via friction generated by the compression.

In Example 5, the subject matter of Example 4 optionally includes a motor coupled to at least one of the at least two rollers via a power transmission unit to drive rotation of the at least two rollers.

In Example 6, the subject matter of Example 4 optionally includes the at least two rollers where the radial outer surface of at least one of the rollers is covered with frictious material.

In Example 7, the subject matter of any one or more of Examples 5-6 optionally includes the at least two rollers where the radial outer surface of at least one of the rollers has a radially concave profile.

In Example 8, the subject matter of Example 5 optionally includes the motor that may be included in the external positioning unit, and the external positioning unit further includes a power source electrically coupled to the motor.

In Example 9, the subject matter of Example 8 optionally includes the power source that may include a rechargeable power source.

In Example 10, the subject matter of Example 5 optionally includes the motor that may be included in the control console. The motor may be coupled to the at least one of the at least two rollers via a shaft running between the control console and the external positioning unit.

In Example 11, the subject matter of any one or more of Examples 2-10 optionally includes first and second motors. The external positioning unit may include first and second coupling units each interfacing with a respective portion of the elongate member of the implant. The first motor, via a first power transmission unit, may be coupled to the first coupling unit to actuate a translational motion of the elongate member. The second motor, via a second power transmission unit, may be coupled to the second coupling unit to actuate a rotational motion of the elongate member.

In Example 12, the subject matter of any one or more of Examples 5-11 optionally includes a manual drive-wheel coupled to at least one of the at least two rollers. The manual drive-wheel is configured to enable manual rotation of the at least one of the at least two rollers.

In Example 13, the subject matter of any one or more of Examples 2-12 optionally includes a sheath extended from the external positioning unit to a surgical entrance of the target implantation site. The sheath may be configured to at least partially enclose the elongate member to provide resilient support to the electrode array during implantation.

In Example 14, the subject matter of any one or more of Examples 1-13 optionally includes an indicator on the external positioning unit to alert a specific implant status.

In Example 15, the subject matter of any one or more of Examples 1-14 optionally includes the external positioning unit that may include a fixation member configured to detachably affix the external positioning unit to the patient.

In Example 16, the subject matter of Example 15 optionally includes the fixation member that may include one or more of a screw, a pin, a nail, a wire, a hook, a suture, or a magnet.

In Example 17, the subject matter of any one or more of Examples 1-16 optionally includes the external positioning unit that may include an exterior patient-contact surface equipped with gripping elements configured to frictionally affix the external positioning unit to the patient.

In Example 18, the subject matter of any one or more of Examples 5-12 optionally includes the controller circuit that may be configured to generate the motion control signal to control the motor to regulate one or more motion parameters of the elongate member/The motion parameters include one or more of: a movement rate; a movement direction or orientation; a movement distance; a position of a distal end of the elongate member; or an amount of force imposed on the elongate member.

In Example 19, the subject matter of Example 18 optionally includes the controller circuit communicatively coupled to the motor via a wired connection.

In Example 20, the subject matter of Example 18 optionally includes the controller circuit communicatively coupled to the motor via a wireless communication link.

In Example 21, the subject matter of any one or more of Examples 1-20 optionally includes the control console that may include a user interface module configured to receive from a user one or more motion parameters. The motion parameters include one or more of: a target movement rate;

a target movement direction or orientation; a target movement distance; a target position of a distal end of the elongate member; or a target amount of force imposed on the elongate member.

In Example 22, the subject matter of Example 21 optionally includes the user interface module that may be configured to receive information about patient tonotopic hearing loss pattern. The controller circuit may be configured to control the external positioning unit to deliver and position at least a portion of the elongate member of the implant further according to the received information about the patient tonotopic hearing loss pattern.

In Example 23, the subject matter of any one or more of Examples 5-12 and 18-20 optionally includes the motion control instruction that may include selectable enabling of a robotic mode for robotically assisted motion control of the elongate member of the implant, or a manual override mode for manual motion control of the elongate member of the implant.

In Example 24, the subject matter of any one or more of Examples 2-13, 18-20 and 23 optionally includes one or more sensors configured to sense one or more motion parameters of the implant during implantation. The control console is configured to control the external positioning unit to propel the elongate member of the implant according to the sensed one or more motion parameters.

In Example 25, the subject matter of Example 24 optionally includes the one or more sensors that may include a Hall-effect sensor configured to sense a position or a displacement of the elongate member of the implant inside the patient.

In Example 26, the subject matter of any one or more of Examples 24-25 optionally includes a force sensor configured to sense an indication of force or friction imposed on the elongate member of the implant during implantation.

In Example 27, the subject matter of any one or more of Examples 24-26 optionally includes the one or more sensors that are included in the external positioning unit.

In Example 28, the subject matter of any one or more of Examples 21-22 optionally includes the user interface module that may include an output module configured to generate a human-perceptible presentation of one or more motion parameters of the implant.

In Example 29, the subject matter of any one or more of Examples 1-28 optionally includes a peripheral control unit communicatively coupled to the external positioning unit or the control console. The peripheral control unit may be configured to control the external positioning unit to propel the implant. The peripheral control unit including one or more of a foot pedal or a handheld device.

Example 30 is a non-implantable apparatus for robotically assisted implantation of a cochlear implant having an electrode array disposed on an elongate member. The apparatus comprises: an external positioning unit including at least two rollers arranged to compress at least a portion of the elongate member between portions of a radial outer surface of each roller of the at least two rollers to transmit translational or rotational forces on the elongate member; wherein at least one of the at least two rollers is coupled to, and driven by, a robotically controlled motor.

In Example 31, the subject matter of Example 30 optionally includes the external positioning unit that may include one or more of: the motor; a power transmission unit interacting with the motor and the at least one of the at least two rollers; or a communicator circuit configured to receive a motion control signal for controlling the motor.

In Example 32, the subject matter of any one or more of Examples 30-31 optionally includes the external positioning unit that may include one or more sensors configured to sense one or more motion parameters of the cochlear implant during implantation.

Example 33 is a method for delivering and positioning an electrode of a cochlear implant on an elongate member into a target implantation site of a patient via an external robotically assisted implantation system. The method comprises steps of: establishing a communication between an external positioning unit and a control console; engaging at least a portion of the elongate member of the cochlear implant to the external positioning unit; affixing the external positioning unit to the patient via a fixation member of the external positioning unit; and robotically controlling the external positioning unit, via the control console, to deliver and position the cochlear implant into the target implantation site.

In Example 34, the subject matter of Example 33 optionally includes the engagement of the elongate member that may include engaging at least a portion of the elongate member of the cochlear implant through compression between respective radial outer surfaces of at least two rollers.

In Example 35, the subject matter of any one or more of Examples 33-34 optionally includes the robotic control of the external positioning unit that may include controlling a motor coupled to the external positioning unit, and regulating one or more motion parameters of the elongate member. The motion parameters may include one or more of: a movement rate; a movement direction or orientation; a movement distance; a position of a distal end of the elongate member; or an amount of force imposed on the elongate member.

In Example 36, the subject matter of any one or more of Examples 33-35 optionally includes sensing one or more motion parameters of the elongate member during implantation, and robotically controlling the external positioning unit to propel the cochlear implant according to the sensed one or more motion parameters.

The systems, devices, and methods discussed in this document may improve the technological field of robotic surgery, particularly robotically assisted implantation of an implant or prosthesis. For example, when the systems or methods discussed herein are used in hearing-preservation cochlear implant surgery, the robotic motion control of the cochlear implant and/or guide sheath may reduce the mechanical forces imposed on the delicate cochlear structure such as basilar membrane and organ of Corti, thereby minimizing the risk of trauma on the undamaged structure such as at the apical cochlea. This may ultimately better preserve patient residual natural hearing. Compared to manual insertion and steering of a cochlear implant, the robotically assisted cochlear implantation may allow more people with disabling hearing loss to hear better over their lifetimes.

The modular design of the robotically assisted implantation system, as discussed in this document, allows for easy replacement or interchange of a particular module. This may not only improve the system reusability and efficiency, but may also reduce the cost of system maintenance. For example, the external positioning unit may be a single-use device positioned in a sterile surgical field or in contact with the patient during an implantation surgery, and is disposable after surgery. The computerized control unit may be positioned in a non-sterile field, such as a control room, and can be reused with interchangeable external positioning units.

The external positioning unit is a non-implanted external device. Compared to a partially or completely implantable insertion device, the external positioning unit discussed herein may substantially reduce the risk of complications associated with surgical implantation, extraction, or replacement of otherwise partially or completely implantable insertion device. The external positioning unit also has the advantage of easy trouble-shooting, maintenance, and replacement, thereby reducing cost of the system and the procedure. As to be discussed in the following, the external positioning unit may have a small size with limited mechanical and electrical parts, thus making it flexible for external fixation to a patient.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

Disclosed herein are systems, devices, and methods for robotically assisted implantation of an implant in a patient. The present system may be implemented using a combination of hardware and software designed to provide precise control of implant movement, such as insertion of a cochlear implant and/or guide sheath during a hearing-preservation cochlear implant surgery. The system includes an external positioning unit configured to engage the implant, and a control console communicatively coupled to the external positioning unit. The control console may have a user interface that enables a user to input motion control instructions. The control console may generate a motion control signal, according to a specific motion control instruction, to control the external positioning unit to propel the implant into a target implant site.

Although the discussion in this document focuses on cochlear implant, this is meant only by way of example and not limitation. It is within the contemplation of the present inventors, and within the scope of this document, that the systems, devices, and methods discussed herein may be configured for robotically delivering, steering, positioning, or extracting various types of implants or prosthesis as well as associated instruments. By way of non-limiting examples, the implants may include leads, catheter, guidewire, guide sheath, or other mechanical or electrical devices. The implants may be designed for temporary or permanent implantation. The implants may be used for medical diagnosis of a disease or other conditions such as diagnostic catheters, or for therapeutic purposes of cure, mitigation, treatment, or prevention of disease, such as implantable electrodes for stimulating cardiac, neural, muscular, or other tissues. In addition to new implantation, the systems, devices, and methods discussed herein may also be used to surgically reposition or replace an existing implant.

Figure 1:
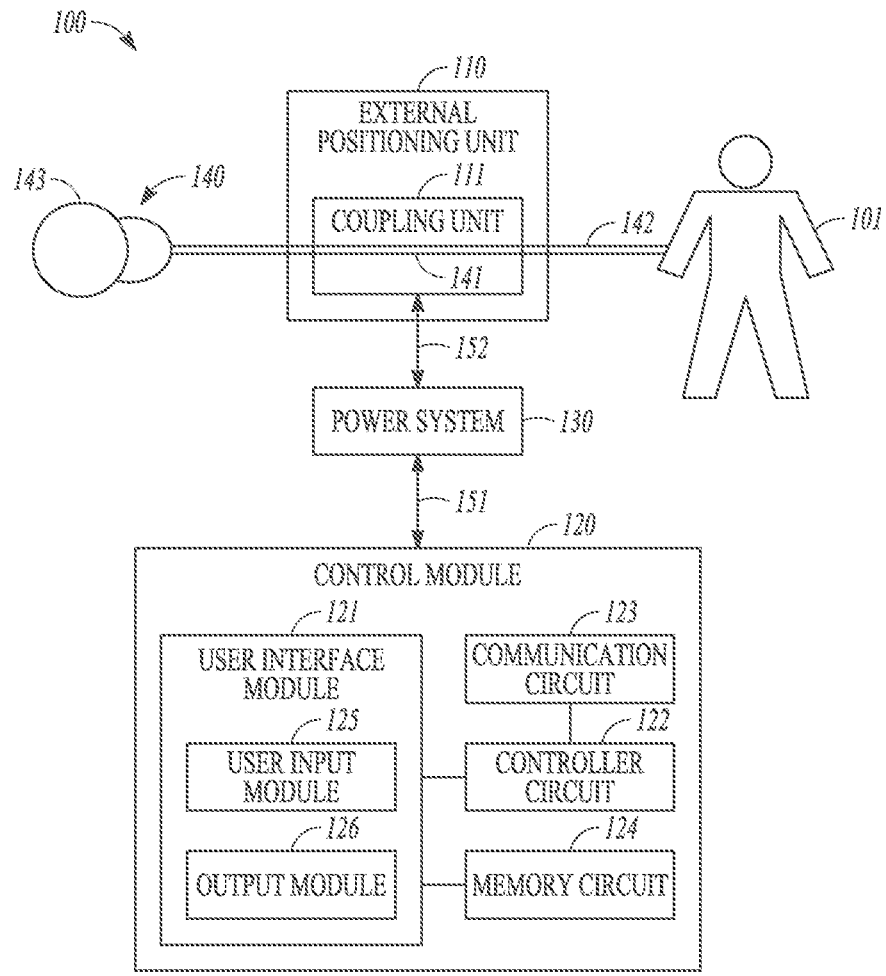
FIG. 1 illustrates, by way of example and not limitation, a robotically assisted implantation system and portions of an environment in which the robotically assisted implantation system may operate.

FIG. 1 illustrates, by way of example and not limitation, a robotically assisted implantation system 100 and portions of an environment in which the system 100 may operate. The robotically assisted implantation system 100 may include an external positioning unit 110 and a control console 120. The robotically assisted implantation system 100 may additionally include a power system 130. The robotically assisted implantation system 100 may engage an implant 140, and robotically deliver and position the implant 140 into a target implantation site of a patient 101.

The implant 140 may include an elongate member 141. The elongate member 141 may be an integral part of the implant 141, such as a tubular implant body or an elongate shaft. Examples of such an implant may include an implantable lead or catheter. Alternatively, the elongate member 141 may be a part of a delivery system detachably coupled to the implant. Examples of such an implant may include a guidewire or an introducer that may snatch an implant at a particular location, such as at a distal portion of the elongate member 141. The external positioning unit 110 may propel the elongate member 141, thereby transporting the attached implant to a target implantation site. Once the implant has reached and been securely positioned at the target implantation site, the elongate member 141 may be disengaged from the implant, and the external positioning unit 110 may retract the elongate member 141 away from the patient 101.

By way of example and not limitation, the implant 140 may include a cochlear implant for treating hearing loss through electrostimulation of a specified cochlea region. The cochlear implant, as illustrated in FIG. 1, may include an implantable stimulator 143 and the elongate member 141 with an electrode array such as disposed at distal portion 142 of the elongate member 141. The implantable stimulator 143, which may be implanted under the scalp, can generate electrical impulses, and deliver the electrical impulses to the electrode array through conductors in the elongate member 141. The electrode array may be surgically inserted into and positioned at the target cochlear site. In patients with impaired high-frequency hearing function but preserved low-frequency hearing function, a short electrode array of the implant may be positioned at the outer or basal cochlear region to deliver electrostimulation therein to restore high-frequency hearing function.

As discussed in further detail below, the implant 140 may be delivered through a guide sheath, which is alternatively or additionally controlled by the external positioning unit 110. In some examples, the external positioning unit 110 includes separate structures to control a guide sheath separately from the implant 140. In other examples, the guide sheath may be positioned initially by the external positioning unit 110, and the implant 140 implanted through the previously positioned guide sheath. In this example, the implant 140 can be controlled by the external positioning unit 140 once the guide sheath is in place.

The external positioning unit 110 is a non-implanted external device. This may substantially reduce the risk of complications associated with surgical implantation of an otherwise implantable implant insertion device. The external positioning unit 110 may include a coupling unit 111 configured to interface with the elongate member 141 of the implant, and frictionally move the elongate member 141 to a specific direction (e.g., forward for implant insertion, or reverse for implant extraction), at a specific rate, or for a specific distance relative to a reference point such as the interface between the coupling unit 111 and the elongate member 141. Examples of the coupling unit 111 may include a leadscrew, a clamp, a set of rotors, or a rack and pinion arrangement, among other coupling mechanisms. The coupling unit 111 may compress against at least a portion of the elongate member 141 to produce sufficient friction between the coupling unit 111 and the elongate member 141. In some examples, the coupling unit 111 may include adjustable couplers for reversible or interchangeable connection between the external positioning unit 110 and the elongate member 141. In the event of implant exchange or replacement, the coupling unit 111 may be adjusted to release the compression on the elongate member 141 of an existing implant, which may be then removed from the external positioning unit 110. A new implant with an elongate member may be reloaded and engaged into the external positioning unit 110. The external positioning unit 110 need not be removed and may remain in place during implant replacement. Examples of the coupling unit 111 are discussed below, such as with references to FIGS. 3A-3C. Examples including positioning of a guide sheath are further discussed in reference to FIGS. 10A-10B.

The external positioning unit 110 is configured to be stably attached to the patient, or to an object at the patient's immediate environment such as the surgical table. In an example, the power system 130 may be separated from, and external to, the external positioning unit 110. The external positioning unit 110 may be a compact, lightweight micromechanical device suitable for direct attachment to the patient, such as on the patient head during a cochlear implant surgery, while maintaining sufficient stability during the implantation. The external positioning unit 110 may be sized and shaped to facilitate patient attachment. In an example, the external positioning unit 110 may have a curved exterior contact surface that conforms to the contour of a body part of the patient 101, such as a head region. In an example, the external positioning unit 110 may include a fixation member to allow for detachable affixation of the external positioning unit 110 to the patient 101. The fixation may be invasive fixation that involves incision of the skin and penetration of subcutaneous tissue. Examples of the fixation member may include one or more of a screw, a pin, a nail, a wire, a hook, a suture, or a magnet within the external positioning unit 110 coupled to one or more magnetic screws or pins affixed to the body part of the patient 101. In an example, the fixation member may include one or more of self-drilling screws, self-tapping screws, or self-piercing screws, such that no pilot hole needs to be drilled at the affixation site prior to screw installation. Alternatively, the fixation may be non-invasive fixation with the use of non-invasive clamps or holding devices that prevent movement relative to the patient 101. In some examples, the external positioning unit 110 may be affixed to at least a portion of the implant 140, such as the implantable stimulator 143. In an example, the affixation may be detachable. By way of non-limiting example, the affixation means may include hooks, clamps, or magnets, among other direct or indirect holding members to prevent relative motion between the external positioning unit 110 and the implant 140. In an example, the external positioning unit 110 may be magnetically affixed to the implantable stimulator 143 which has a magnet within. In various examples, the implant 140 may include communication coils for data communication with the external positioning unit 110 and the control module 120. The magnetic coupling between the external positioning unit 110 and the implant 140 as discussed herein may allow the communication coils within the implant 140 to be aligned with communication antenna coils within the external positioning unit 110 to communicate, receive, or transmit data to and from the underlying implant 140, such as for transmitting electrophysiological data acquired from the patient 101.

The contact surface of the external positioning unit 110 may be processed to improve stability during the implant advancement procedure. In an example, the external positioning unit 110 may have an exterior surface with a rough finish, such as ridges, corrugates, teeth, or other coarse surface textures. Additionally or alternatively, the external positioning unit 110 may have one or more gripping elements configured to frictionally bond the external positioning unit 110 to a body part of the patient 101. The gripping elements may be distributed on a portion of the exterior surface. Examples of the gripping elements may include penetrators such as spikes, pins, or barbs protruding from the exterior surface. When the external positioning unit 110 is pressed and held against the attachment region (e.g., patient head), the rough surface or the gripping elements may provide sufficient friction or gripping force to securely hold the external positioning unit 110 in place relative to the patient 101 during the implantation advancement.

The control console 120 may include a dedicated hardware/software system such as a programmer, a remote server-based patient management system, or alternatively a system defined predominantly by a controller software running on a standard personal computer. The control console 120 may robotically control the coupling unit 111 to propel the elongate member 141 at specific rate, to a specific direction, or for a specific distance, or at a specific maximum force, thereby delivering and positioning the implant 140, such as an electrode array of a cochlear implant, at the target implantation site of the patient 101. The control console 120 may additionally receive information acquired by sensors disposed on the motor system 130 or the external positioning unit 110, as to be discussed in the following. The control console 120 may also receive measurement data from external systems that can be directly related to implant position. The control console 120 can utilize such measurement data (e.g., electrophysiological measurements) for closed loop control of implant positioning. In addition to sensing motion parameters, electrophysiological measures can be linked to system controller through software interfaces or means for inputting to control system in real-time measures such as electrocochleography (ECoG), neural response telemetry, cochlear response telemetry, or auditory brainstem responses (ABRs) recordings from either the cochlear implant or other ECoG recording system or method.

The control console 120 may control the external positioning unit 110 via a power system 130. The power system 130 includes a motor that may generate driving force and motion, and a power transmission unit to transmit the driving force and motion to the coupling unit 111 to actuate the motion of the elongate member 141. The power transmission unit may include one or more of chains, belts, gears, or shaft couplings, among others. In an example, the power system 130 may be separated from the external positioning unit 110 and the control console 120, and coupled to the coupling unit 111 via a connection 152. The connection 152 may be a part of the transmission unit. In another example, the power system 130 may be at least partially included in or associated with the external positioning unit 110. In yet another example, the power system 130 may be at least partially included in or associated with the control console 120. Examples of the power system 111 are discussed below, such as with references to FIG. 2.

The control console 120 may include a user interface module 121 and a controller circuit 122. The user interface module 121 may include a user input module 125 and an output module 126. The user input module 125 may be coupled to one or more input devices such as a keyboard, on-screen keyboard, mouse, trackball, touchpad, touchscreen, or other pointing or navigating devices. In some example, the user input module 125 may be incorporated in a mobile device communicatively coupled to the control console 120, such as a handheld device. The user input module 125 may be configured to receive motion control instructions from a user. The motion control instructions may include one or more target motion parameters characterizing desired movement of the elongate member 141 of the implant. For example, the target motion parameters may define maximum values or value ranges of the motion parameters. Examples of the target motion parameters may include a target movement rate, a target movement direction or orientation, a target movement distance, a target position of a distal end of the elongate member, or a target amount of force imposed on the elongate member 141. The movement of the implant may be activated at intervals of a predetermined step size. In an example of implantation of a cochlear implant, the target movement rate is approximately at 100-micron intervals. In an example, the target movement distance is approximately 1-35 millimeters. The motion control instructions may include a pre-determined implant delivery protocol that defines target values of a plurality of motion parameters. The implant delivery protocols are designed to ease the programming of the motion control, and to minimize peri-surgical tissue trauma or damage to the implant.

The user interface module 121 may allow a user to select from a menu of multiple implant delivery protocols, customize an existing implant delivery protocol, adjust one or more motion parameters, or switch to a different implant delivery protocol during the implant delivery procedure. The control console may include a memory circuit 124 for storing, among other things, motion control instructions. In an example, one of the delivery protocols may include use intraoperative ECoG measures such as cochlear microphonics (CM), auditory nerve neurophonics (ANN) that can reflect immediate changes in the cochlear mechanics and insertion trauma pre-, during-, and post-insertion of the electrode array. Use of discussed in further detail below in reference to FIGS. 6 and 9

The output module 126 may generate a human-perceptible presentation of information about the implant delivery control, including the programmable motion control parameters, and the motion control instructions provided by the user. The presentation may include audio, visual, or other human-perceptible media formats, or a combination of different media formats. The output module 126 may include a display screen for displaying the information, or a printer for printing hard copies of the information. The information may be displayed in a table, a chart, a diagram, or any other types of textual, tabular, or graphical presentation formats. Additionally or alternatively, the output module 126 may include an audio indicator such as in a form of beeps, alarms, simulated voice, or other sounds indicator.

The robotically assisted implantation system 100 may comprise one or more sensors configured to sense one or more motion parameters of the implant during implantation. The output module 126 may generate a human-perceptible presentation of the sensor feedback, including one or more parameters on the position of the implant, motion of the implant, or the force or friction applied to the implant motion. This allows a surgeon to monitor in real time the progress of the implantation, and adjust the motion control as needed. The presentation may include real-time visual or audible notification with specified patterns corresponding to different types of events encountered during implantation. In an example, the output module 126 may include a visual indicator, such as a light emitting diode (LED) or an on-screen indicator on the display screen. A specific LED color or a specific blinking pattern may signal to the user a successful positioning of the implant at the target implantation site. A different LED color or a different blinking pattern may alert an excessive force imposed on the implant due to unintended tissue resistance during the implant advancement. The output module 126 may additionally or alternatively include an audio indicator, such as a beep with a specific tone, a specific frequency, or a specific pattern (e.g., continuous, intermittent, pulsed, sweep-up, or sweep-down sound). In an example, a beep or an alarm with a specific tone or pattern may signal to the user successful positioning of the implant at the target implantation site. A beep or an alarm with a different tone or different pattern may alert an excessive force imposed on the implant. In an example, the beep or the alarm may go off continuously as the sensor senses the implant approaching the target site. The sound frequency or the pulse rate of the beep or the alarm may increase as the implant gets closer and finally reaches the target site. In an example, the frequency of the beep or the alarm may correspond to a rate of motion, such as sounding for every one millimeter of motion. Audible feedback on the motion parameters may be advantageous in that the surgeon may be notified in real time the implantation status or events encountered without the need to look away from surgical field. This may assist surgeon with enhanced surgical precision and patient safety. In some examples, the audible or visual sensor feedback may signal to the user that the sensed implant position, motion, or for has exceeded the programmed target or maximum parameter values.

The controller circuit 122 may be configured to generate a motion control signal according to the motion control instructions provided by the user via the user input module 125. The motion control signal may control the power system 130 to regulate one or more motion parameters of the elongate member 141. Examples of the motion parameters may include a movement rate, a movement direction or orientation, a movement distance, a position of a distal end of the elongate member, or an amount of force imposed on the elongate member 141, among others. In an example where the power system 130 is separated from and external to the control console 120, the controller circuit 122 may remotely control the power system 130 via a communication circuit 123. The communication circuit 123 may transmit the motion control signal to the power system 130 via the communication link 151. The communication link 151 may include a wired connection including universal serial bus (USB) connection, or otherwise cables connecting the communication interfaces on the control console 120 and the power system 130. The communication link 151 may alternatively include a wireless connection, such as a Bluetooth protocol, a Bluetooth low energy protocol, a near-field communication (NFC) protocol, Ethernet, IEEE 802.11 wireless, an inductive telemetry link, or a radio-frequency telemetry link, among others.

In some examples, the controller circuit 122 may control the motion of the elongate member 141 further according to information about patient medical history or disease state received via the user input module 125, or stored in the memory circuit 124. In an example of cochlear implant, information about patient tonotopic hearing loss pattern. The tonotopic hearing loss pattern represents a spatial distribution of frequency sensitivity along the axis of the cochlea length. Based on the input of the patient tonotopic hearing loss pattern, the controller circuit 122 may automatically program one or more motion parameters, such as the electrode array insertion distance. For example, for a patient with a tonotopic pattern of high-frequency insensitivity and preserved low to medium-frequency sensitivity, a shorter cochlear implant insertion distance is indicated. The electrode array of the cochlear implant may be positioned and electrically stimulate the outer or basal cochlear region to restore high-frequency hearing. Conversely, for a patient with a tonotopic pattern of high-frequency insensitivity as well as deteriorated low to medium-frequency hearing, a longer insertion distance is indicated. The electrode array of the implant may be positioned to stimulate a wider cochlear region that covers the outer or basal region as well as certain inner or apical cochlear region. The tailoring of the implant motion parameters (such as the implant insertion distance) based patient tonotopic pattern enables an individualized treatment regimen to achieve improved therapy outcome, and can best fit a patient's evolving hearing loss. It may expand candidacy range, qualifying more people for cochlear implant therapy.

In an example, the controller circuit 122 may control the motion of the elongate member 141 further according to ECoG measures received. A real-time link to ECoG measure during implant insertion enables notification of potential physiological injury to intracochlear structures, such as contact with the basilar membrane. If decreases or significant changes are recorded in ECoG measures, the controller circuit 122 can provide immediate feedback to the surgeon, through the user interface module 121, in the form of visual or audible notifications and a stop command may be sent to the system controller to prevent further implant motion. Optionally, the controller circuit 122 can be programmed to automatically stop or reverse the insertion upon detection of certain ECoG measurement signatures. After the system notification to the user or automatic intervention, the surgeon may adjust implant insertion trajectory or system motion parameters as needed to avoid intracochlear damage or suboptimal electrode position or choose to the override notifications via physical acknowledgement mechanism. After acknowledgment of warning notification, the stop feedback is removed and the user may continue robotic-assisted insertion of the implant.

The external positioning unit 110 may include a manual control mechanism in addition to the robotic control of the coupling unit 111. The manual control mechanism may bypass or override the robotic motion control of the implant 140. Examples of the manual control mechanism may include a dial turn, a screw, or direct insertion technique. The output module 126 may enable a user to selectably enable a robotic mode for robotically assisted motion control via the power system 130, or a manual override mode for manual motion control of the elongate member 141. Alternatively, an operation on the manual control mechanism may automatically withhold or disable the robotic motion control of the elongate member 141. Examples of the manual control of the external positioning unit are discussed below, such as with references to FIG. 5.

Portions of the control console 120 may be implemented using hardware, software, firmware, or combinations thereof. Portions of the control console 120 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
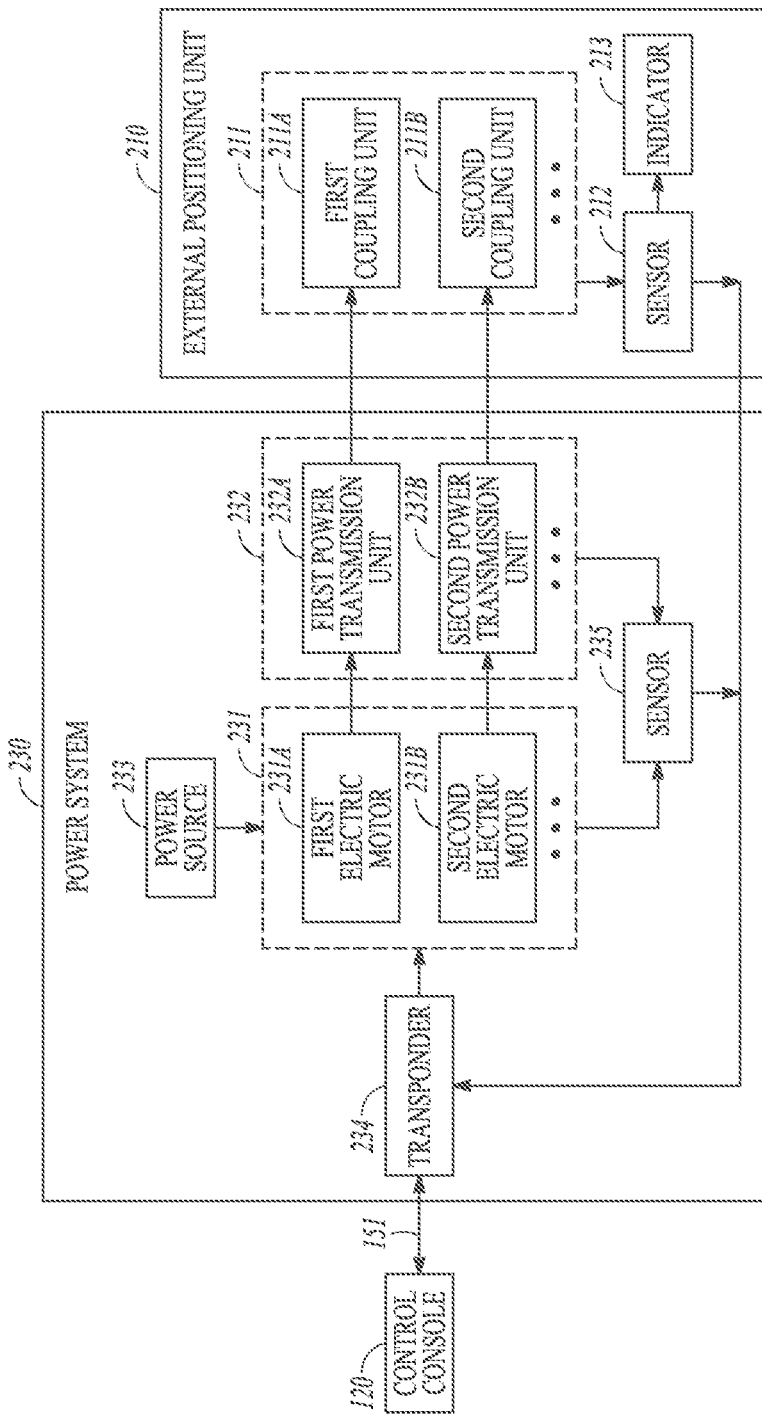
FIG. 2 illustrate, by way of example and not limitation, a block diagram of a power system that provides driving force and motion to the external positioning unit to propel and position an implant.

FIG. 2 illustrate, by way of example and not limitation, a block diagram of a power system 230 that provides driving force and motion to the external positioning unit 210 to deliver and position an implant. The power system 230 may be an embodiment of the power system 130 of the robotically assisted implantation system 100 as illustrated in FIG. 1. The power system 230 may provide a one-degree of freedom, or multiple-degrees of freedom, control over the elongate member 141 of the implant.

The power system 230 may include one or more electric motors 231 each coupled to respective power transmission units 232. The one or more power transmission units 232 are each coupled to respective coupling units 211 in the external positioning unit 210, which is an embodiment of the external positioning unit 110 as illustrated in FIG. 1. The one or more electric motors 231 may be electrically coupled to a power source 233. In an example, the power source 233 may include a rechargeable power source, such as a rechargeable battery or a supercapacitor. The rechargeable power source may be charged wirelessly by a portable device such as a handheld device with circuitry configured to transfer energy to the rechargeable power source through electromagnetic induction.

The one or more electric motors 231 may be of the same or different types of motors. Examples of the electric motors 231 may include stepper motors, direct current (DC) motors, piezo electric motors, ultrasonic motors, or linear motors, among others. The one or more electric motors 231 may each be coupled to a transponder 234 that may receive motion control signals from the control console 120 via the communication link 151. The control console 120 may generate respective motion control signal for each of the electric motor 231 according to the motion control instructions provided by the user. In an example, a user may independently program (by inputting the motion control instructions) and control the operation of each of the electric motors 231, such as via the user input module 125. The motion control signal specify the configurations and input voltage or current to the respective electric motor 231, which may generate the desired torque, speed, or rotation direction.

In response to the received motion control signal, the one or more electric motors 231 may generate respective driving force and motion that control various motion parameters of the elongate member 141 of the implant via the power transmission unit 232. The power transmission units 232 may adjust the speed or torque output from the motors, and to deliver specific output to the respective coupling units 211. Examples of the power transmission units 232 may include spur gears, helical gears, planetary gears or gearhead, worm gears, miniature pulleys, or timing belts, among others.

By way of example and not limitation, and as illustrated in FIG. 2, the electrical motors 231 may include at least a first electric motor 231A and a second electric motor 231B. The first electric motor 231A may generate driving force and motion, transmitted to the first coupling unit 211A via the first power transmission unit 232A, to control one or more parameters associated with a motion along a first orientation, such as a translational motion. Examples of the translational motion parameters may include movement rate, direction, distance relative to a reference point, a position of a distal end of the elongate member, or an amount of axial force applied to the elongate member. The second electric motor 231B may generate driving force and motion that is transmitted to the second coupling unit 211B via the second power transmission unit 232B, and control one or more parameters associated with a motion along a second orientation, such as a rotational motion. Examples of the rotational motion parameters may include angular position, angular displacement, angular velocity, or an amount of lateral or rotational force applied to the elongate member. The first and second electrode motors, along with the respective power transmission units and the coupling units in the external positioning unit, may provide a flexible and precise control of the motion of the implant on multiple degrees of freedom. This may allow for optimal positioning of the implant at the target implantation site, such as placement of cochlear implant electrode array in close proximity to auditory nerve cells and neurons.

One or more sensors may be configured to sense information about position and motion of the implant during implantation, such as a sensor 235 in the power system 230, or a sensor 212 in the external positioning unit 210. In an example, one or more linear or rotary encoders may be attached to the electric motor 231, the power transmission unit 232, or the coupling units 211 to detect the information about position of the implant. In another example, one or more Hall effect sensors may be integrated in the electric motor 231. In yet another example, one or more optional sensors may be attached to the coupling unit 211. In some examples, the sensor 235 or the sensor 212 may include capacitive sensors configured to detect implant motion.

In addition to or in lieu of the motion and position sensing, the sensor 235 or the sensor 212 may include force sensors to sense a parameter indicative of force or friction imposed on the implant during the implant advancement, such as axial, lateral, or radial forces when the cochlear implant interacts with cochlea wall and surrounding tissues. Examples of the force sensors may include resistors, capacitive sensors, piezoelectric material, or a strain gauge, among others. In an example, the force may be indirectly sensed by measuring the current supplied to the electric motor 231. The current measurement may be transmitted to the control console 120, where it is converted to the force (or torque) using the torque-current curve predetermined and stored in the memory circuit 124.

The information acquired by the sensors 235 and the sensors 212 may be forwarded to the control console 120 via the communication link 151. The sensor information may be displayed or otherwise presented in a specific media format in the output module 126. In an example, the external positioning unit 210 may include an indicator 213 coupled to the sensor 212. The indicator 213 may produce a visual or audio notification in response to the sensed sensor signal satisfies a specific condition. In an example, the indicator 213 may include a light emitting diode (LED) that may be turned on when the sensed sensor signal indicates the implant reaches the target implantation site. In some examples, the indicator 213 may include a plurality of LEDs with different colors or different pre-determined blinking patterns. The LED colors or the blinking patterns may correspond to various events encountered during the implantation procedure.

The control console 120 may generate and modify the motion control signal based on user input of motion control instructions to control the motion of the elongate member of the implant. Alternatively, the control console 120 may automatically adjust the motion control according to the sensed motion parameters. In an example, if the sensed force imposed on the implant exceeds a threshold value, the control console 120 may automatically halt the ongoing motion of the implant or reduce the speed of motion. An alert may be generated and presented on the output module 126. This may be a programmable safety mechanism to prevent unintended tissue trauma or damage to the implant. If the implant movement distance has reached a pre-determined target movement distance, the control console 120 may automatically withhold the motion of the implant.

Figure 3A:
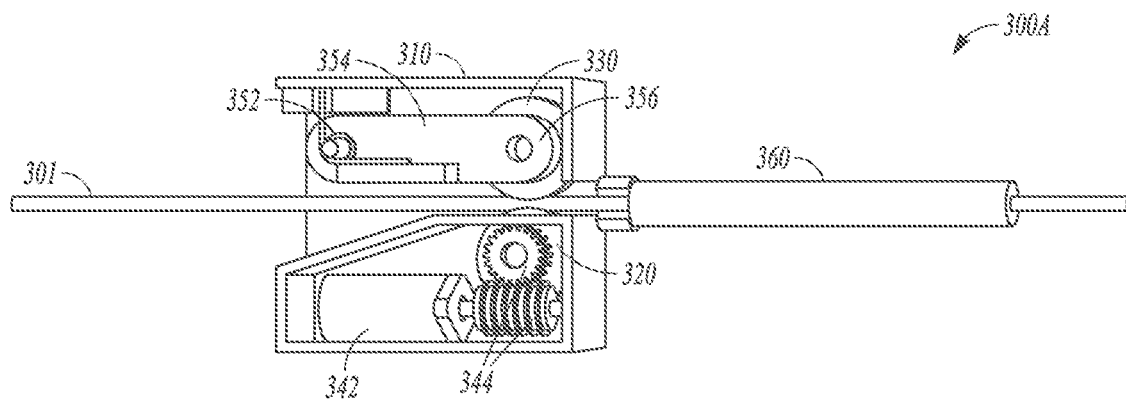
FIGS. 3A-3C illustrate, by way of example and not limitation, diagrams of external positioning units each coupled to an elongate member of an implant.
Figure 3B:
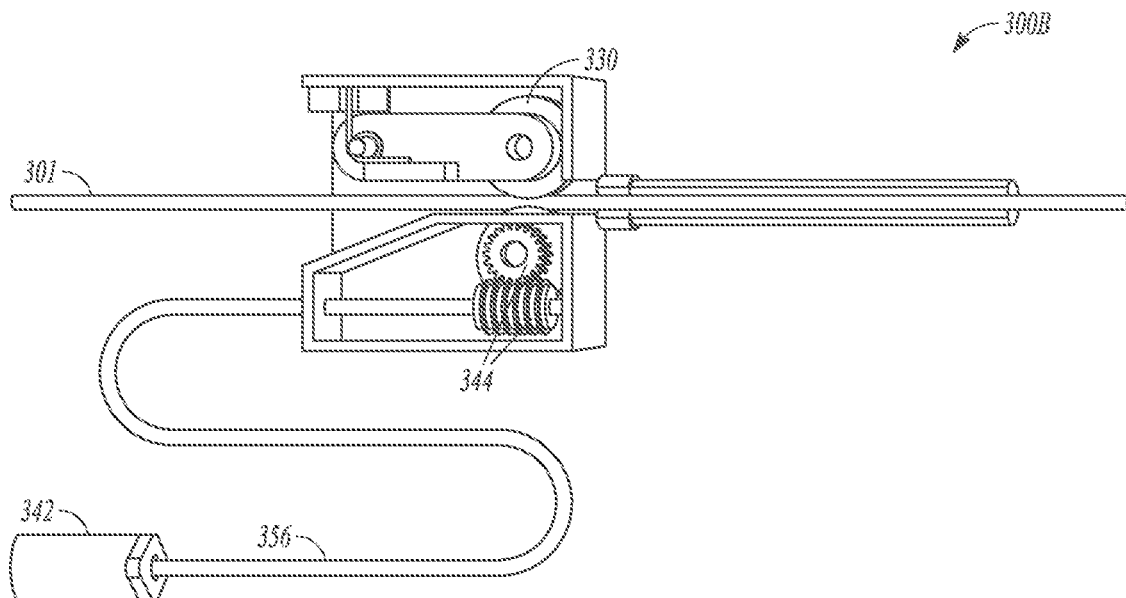
Figure 3C:
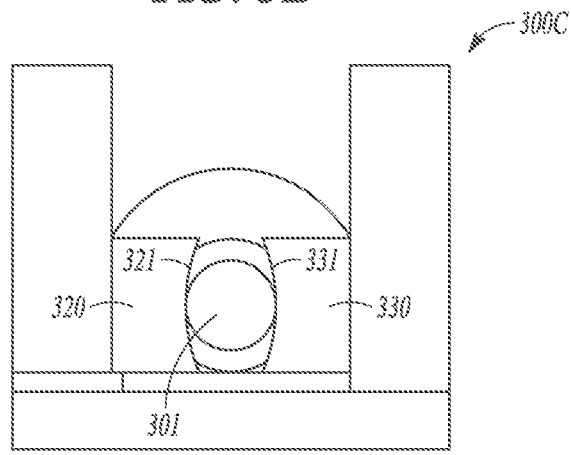

FIGS. 3A-3C illustrate, by way of example and not limitation, diagrams of external positioning units 300A and 300B each coupled to an elongate member 301 of an implant. The elongate member 301, which is an embodiment of the elongate member 141, may be a part of a cochlear implant that includes an electrode array disposed on the elongate member 301. The external positioning units 300A and 300B are embodiments of the external positioning unit 110 as illustrated in FIG. 1.

The external positioning unit 300A illustrated in FIG. 3A includes a housing 310 that encloses electro-mechanical components interconnected to engage the elongate member 301 and robotically deliver and position the implant attached to the elongate member 310 into a target implantation site. The housing 310 may include an entrance and an exit ports to feed the elongate member 310 through the external positioning unit 300A. The external positioning unit 300A may include at least two rollers, such as a drive wheel 320 and an idler wheel 330, which are embodiments of the coupling unit 111 or 211. The drive wheel 320 and the idler wheel 330 are arranged and configured to engage at least a portion of the elongate member 301. The engagement of the elongate member 301 may be through compression between respective radial outer surfaces of the drive wheel 320 and an idler wheel 330.

The drive wheel 320 may be coupled via a bearing to an axle that is securely attached to the housing 310, such that the drive wheel 320 may rotate on the axle without lateral movement relative to the housing 310. The drive wheel 320 may be coupled to an electric motor 342 via a power transmission unit 344. The electric motor 342, which is an embodiment of one of the electric motor 231, may generate driving force and motion according to a motion control signal provided by the control console 120. The electric motor 231 may be coupled to the power transmission unit 344, which may be an embodiment of one of the power transmission unit 232. The power transmission unit 344 may include gears, pulleys, or timing belts that adjust a speed or torque of the motors. In an example as illustrated in FIG. 3A, the power transmission unit 344 may include a worm gear set 344 comprising a worm gear, and a shaft securely coupled to a gearhead of the electric motor 342. Depending on the motion control signal input to the motor 342, the power transmission unit 344 may drive rotation of the drive wheel 320, which in turn propels the implant to a specific direction (e.g., forward or backward) or at specific rate.

The idler wheel 330 may be coupled to a biasing system that includes a torsion spring 352, a pivot arm 354, and a spring bias 356 interconnected to support the second wheel 330 and to provide lateral compression against the drive wheel 320. The torsion spring 352 may produce spring tension relayed to the second wheel 310 via the pivot arm 354, and compress against the drive wheel 320 to generate adequate friction on the elongate member 301 between the drive wheel 320 and the idler wheel 330. Because the idler wheel 330 is held in place by the biasing system rather than being affixed to the housing 310, the idler wheel 330 may move laterally relative to the housing 310. This may allow for accommodating implants with elongate members of a range of diameters or cross-sectional shapes, while maintaining sufficient friction on the elongate member for desirable movement. In an example, a user may manually bias the torsion spring 352 and move the idler wheel 330 away from the drive wheel 320, thereby release the compression and open the space between the drive wheel 320 and the idler wheel 330. The surgeon may remove the elongate member 301 from the external positioning units 300A, or load another implant with an elongate member into the external positioning units 300A.

In some examples, the radial outer surface of the drive wheel 320 may be coated with a frictious material, such as a layer of silicone rubber, polymer, or other composite materials. Additionally or alternatively, the radial outer surface of the drive wheel 320 may be mechanically textured to have a rough and corrugated surface. The frictious material layer or the corrugated surface finish of the radial outer surface of the drive wheel 320 may increase the friction and prevent the elongate member 301 from slipping on the drive wheel 301 during frictional motion. The radial outer surface of the idler wheel 330 may similarly be coated with the frictious material or have a rough surface finish.

FIG. 3C illustrates a cross-sectional view 300C of the drive wheel 320 and the idle wheel 330 with the elongate member 301 engaged therebetween. In an example as illustrated in 300C, the elongate member 301 has a cylindrical shape or otherwise has a convex cross-sectional profile. The radial outer surface 321 of the drive wheel 320 and the radial outer surface 331 of the idle wheel 330 may each have a radially concave profile to allow for secure engagement of the elongate member 301. The concavity of the concave profile, which quantifies a degree of the concave surface, may be determined based on the geometry such as the diameter of the elongate member 301.

The drive wheel 320 and the idler wheel 330 illustrated in FIG. 3A may generate one-degree of freedom of movement, such as a translational motion. In some examples, the external positioning unit 300A may include additional wheels or gear sets arranged and configured to translate the force and motion generated from the motor 342 into multiple-degrees of freedom movement, as previously discussed with reference to FIG. 2. In an example, the external positioning unit 300A may include a gear set to translate the motor motion into a rotational motion of the elongate member 301 around its axis. The gear set may include a geared drive wheel coupled to a worm gear coaxially disposed along, and detachably coupled to, a portion of the elongate member 301. The geared drive wheel, when driven to rotate by the motor 342 and the power transmission unit 344, may drive rotation of the worm gear, which in turn cause the rotation of the elongate member 301 around its axis.

The drive wheel 320 and the spring-biased idler wheel 330 are an example of the coupling unit by way of illustration and not limitation. An alternative coupling unit may include a geared drive wheel coupled to an implant carrier. The carrier may include an adapter housing placed over and securely hold the elongate member of the implant. The adapter housing may be made of silicone or metal. The carrier may have a linear gear arrangement with teeth configured to engage with the geared drive wheel. The geared drive wheel and the linear gear of the carrier may thus have a rack-and-pinion arrangement, where the geared drive wheel (the pinion) applies rotational motion to the linear gear (the rack) to cause a linear motion relative to the pinion, which in turn may linearly move the elongate member held within the adapter housing of the carrier.

One or more sensors may be attached to the internal components of the external positioning unit 300A, such as the electric motor 342, the power transmission unit 344, the drive wheel 320, or the spring-biased idler wheel 330. Examples of the sensors may include an encoder or a Hall effect sensor. The sensors may sense the location or motion of the elongate member 301, or the force or friction applied to the elongate member 301. In an example, a first sensor may be attached to the motor 342 to detect the motion of the motor (which indicates the position or motion of the elongate member 301), and a second sensor may be attached to the idler wheel 330 to detect the motion of the idler wheel (which also indicates the position or motion of the elongate member 301). The first and second sensors may jointly provide a double check of the implant's position, and can more reliably detect any slippage that may occur between the drive wheel 320 and the elongate member 301. For example, if the motor 342 functions normally but the elongate member 301 slips on the drive wheel 320, the first position sensor on the motor would indicate implant movement, but the second position sensor on the idler wheel 330 would indicate no movement or irregular movement of the implant. The control console 120 may include circuitry to detect a discrepancy between the position or motion feedbacks from the first and second sensors. If the discrepancy exceeds a specific threshold, the control console 120 may generate an alert of device fault and presented to the user via the output module 126, or automatically halt the implantation procedure until the user provides instructions to resume the procedure.

The external positioning unit 300A may include a sheath 360. The sheath 360 may be attached to a distal end of the housing 310, and extend to a surgical entrance of the target implantation site. The elongate member 301 may be flexible and prone to twisting, entanglement, or buckling. The sheath 360 may at least partially enclose the elongate member 301 to provide resilient support to the elongate member 301 of the implant, thereby keeping the implant on track between the housing 310 and the surgical entrance of the target implantation site. It may also protect electronics such as an electrode array positioned on the elongate member 301 and the conductors inside the elongate member 301.

The sheath 360 comprises a flexible tube whose dimensions may substantially match the elongate member 301. For example, the diameter of the tube may be slightly greater than the diameter of the elongate member 301, such that the flexible tube may provide desired rigidity to the elongate member 301 inside; while at the same does not produce undue friction between the elongate member 301 and the interior surface of the tube. To decrease friction produced by the motion of the elongate member 301 relative to the tube during implantation, the sheath 360 may be pre-lubricated with a biocompatible and sterilizable lubricant. Alternatively or additionally, the interior surface of the tube may be treated with Polytetrafluoroethylene (PTFE) or linear longitudinal ridges to allow for smooth sliding of the elongate member 301 inside the tube.

The distal end of the sheath 360 may be fixed or reversibly stabilized at a designated position of the surgical opening of the implantation. In an example of cochlear implant, the distal end of the sheath 360 may be stabilized at the cochlea round window (RW) or cochleostomy site by closely matching tube diameters to the RW niche or cochleostomy dimensions. This would allow the sheath 360 to be compressed into the RW niche, or temporarily through the RW membrane. The sheath 360 may be made of material with low friction, such as plastic or silicone rubber, and biocompatible for tissue contact and compatible with various disposable sterilization methods such as radiation (e.g., gamma, electron beam, or X-ray), or ethylene oxide gas treatment. The sheath 360 may be detached from the implant once the implant is positioned at the target site of implantation. Examples of the disengagement means for separating the sheath 360 from the implant are discussed below, such as with reference to FIGS. 4A-4C.

In some examples, the external positioning unit 300A may be affixed to the patient or an object in the sterile field of surgery. The components inside the external positioning unit 300A, including the drive wheel 320, the idler wheel 330, the idler wheel biasing system (including the torsion spring 352, the pivot arm 354, and the spring bias 356), and the power system (including the electric motor 342 and the power transmission unit 344), may be made of materials that are both biocompatible and compatible with a specific sterilization method, such as gamma or ethylene oxide. The electro-mechanical components may be made of plastic such as Acrylonitrile-Butadiene-Styrene (ABS), Polycarbonate, Polyetheretherketone, or Polysulfone, among others. The electro-mechanical components may alternatively be made of metal such as stainless steel, cobalt chromium, or titanium, among others.

The external positioning unit 300B as illustrated in FIG. 3B has a similar structure to the external positioning unit 300A, except that the electric motor 342 is positioned outside the housing 310. The force and motion generated from the electric motor 342 may be transmitted to the drive wheel 320 via a flex rotating shaft 356 running between the motor 342 and the external positioning unit 300B. In an example, the electric motor 342 may be enclosed in stand-alone housing separated from the external positioning unit 300B and the control console 120. In another example, the electric motor 342 may be included in or associated with the control console 120. The flex rotating shaft 356 may be integrated with a communication cable linking the external positioning unit 300B and the control console 120, such that a single cable exits the positioning unit 300B. The communication cable may transmit the sensor feedback on the position or motion of the elongate member 301, or the forces imposed on the elongate member 301 such as sensed by one or more sensors on the positioning unit 300B, such as illustrated in FIG. 2.

With the exclusion of the electric motor 342, the external positioning unit 300B may offer several benefits. The external positioning unit 300B may be a smaller, simpler, light-weighted, and low-cost micromechanical device. As the electric motor 342 and associated electrical system are away from direct patient contact and outside of the patient immediate environment, the external positioning unit 300B may offer an increased patient safety. The external positioning unit 300B may be for single use in a sterile surgical field, and is disposable after the surgery. At least due to its small size and lightweight, the external positioning unit 300B may be suitable for fixation on a patient as a stable platform for advancing the implant.

Figure 4A:
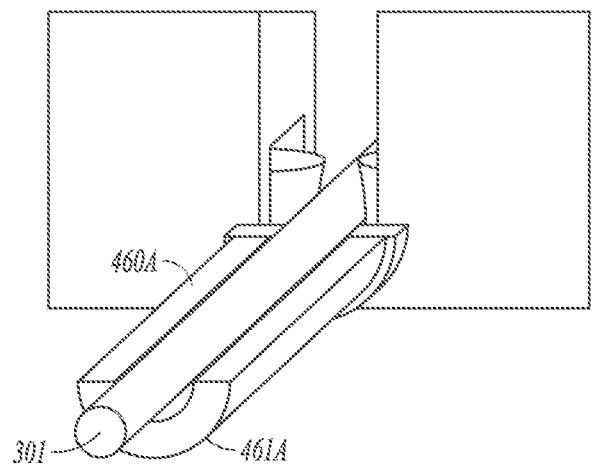
FIGS. 4A-4C illustrates, by way of example and not limitation, disengagement means for separating implant introducer sheath from the elongate member of an implant.
Figure 4B:
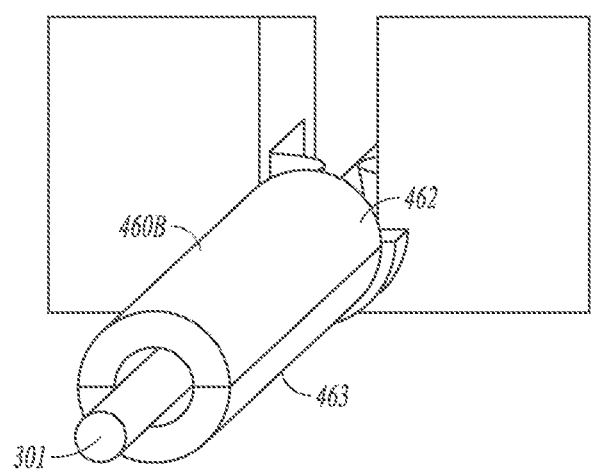
Figure 4C:
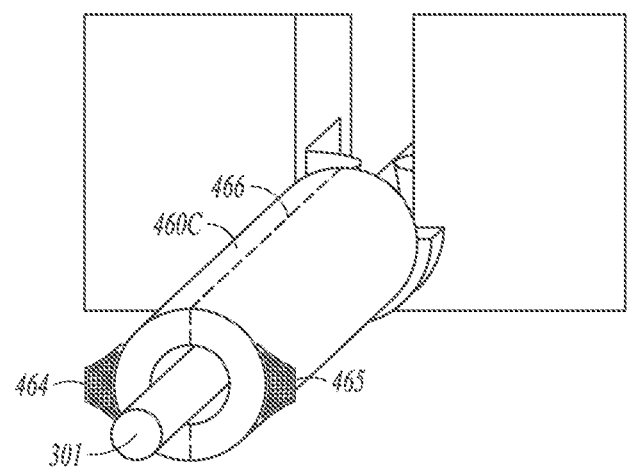

FIGS. 4A-4C illustrates, by way of example and not limitation, disengagement means for separating implant introducer sheath 460A-460C from the elongate member 301 of an implant when the implant is positioned at the target site of implantation. The introducer sheath 460A-460C are embodiments of the sheath 360 as illustrated in FIGS. 3A-3B. The disengagement means may detach the elongate member 301 from the introducer sheath 46A-460C without imposing damaging forces on the implant such as to prevent dislodgement of the implant from the implantation site upon removal of the sheath 360. In a hearing-preservation cochlear implant surgery, for example, once an electrode array of the cochlear implant has been positioned at a desired cochlear region (e.g., the basal cochlea) for stimulating the auditory nerves therein, a surgeon may separate the introducer sheath 460A-460C from elongate member 301 using the disengagement means without cause dislodgement of the electrode array or any trauma to the nearby cochlear tissue.

FIG. 4A illustrates an example of an introducer sheath 460A having a cross section 461 with a shape of a semi-circle or a minor arc, and an open portion along its trajectory. The open portion may be sized such that the elongate member 301 stays stably embedded inside the sheath 460A during implantation, and can easily be pulled out afterwards. Such a sheath with an open portion may achieve a balance between the size of the open portion and the relative difference in durometers of the sheath and implant materials.

FIG. 4B illustrates an example of an introducer sheath 460B that includes two longitudinal halves running in parallel, such as a top piece 462 and a bottom piece 463. The two longitudinal halves are detachably affixed to each other. As illustrated in FIG. 4B, the top and bottom pieces 462 and 463 may each have a semi-circle shape (i.e., 180-degree arc). Alternatively, one piece may be shaped as a minor arc (i.e., less than 180 degrees) and the other shaped as a major arc (i.e., greater than 180 degrees). The two longitudinal halves may be connected with a biocompatible and sterilization-resistant adhesive or sealant. The adhesive or sealant may have an adhesion strength sufficient to hold the two longitudinal pieces together, and may be weakened under a pulling stress. After the implant is being positioned at the desired implantation site, the two longitudinal halves may be disengaged from each other under pulling stress by a surgeon, thereby separating the elongate member 301 from the top and bottom pieces 462 and 463.

FIG. 4C illustrates an example of an introducer sheath 460C configured as a peel-away sheath. The introducer sheath 460C may include dual knobs or release tabs 464 and 465 attached to the circumferential surface of the elongate member 301, such as at a distal portion of the elongate member 301. The dual knobs or the release tabs 464 and 465 may be sized and shaped to allow for a user, by using a surgical tool such as forceps, to peel away the introducer sheath 460C after the implant is positioned at the target implantation site. The introducer sheath 460C may have linear perforations 466 on opposing longitudinal sides to facilitate the tearing of the introducer sheath 460C into two opposing pieces.

Figure 5:
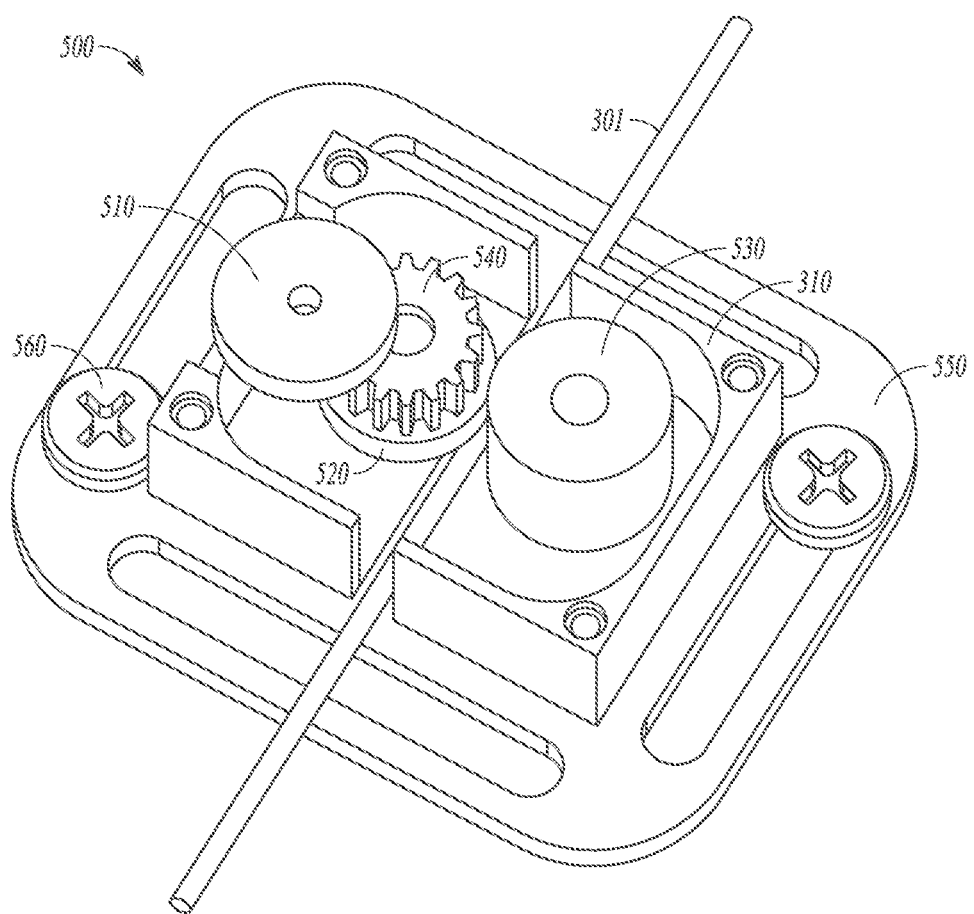
FIG. 5 illustrates, by way of example and not limitation, a portion of an external positioning unit configured to enable manual control over the motion of the implant.

FIG. 5 illustrates, by way of example and not limitation, a portion of an external positioning unit 500 configured to enable manual control over the motion of the implant. The external positioning unit 500, which may be an embodiment of the external positioning unit 110 or 210, may include mechanics enclosed in a housing 310 attached to a base 550. The base 550 may be detachably affixed to the patient or an object on the patient immediate environment via a fixation member 560 such as screws, pins, nails, wires, hooks, a suture, or a magnet, as discussed with reference to FIG. 1. Similar to the external positioning units 300A or 300B as illustrated in FIGS. 3A-3B, the illustrated portion of the external positioning unit 500 comprises at least two rollers, including a drive wheel 520 and an idler wheel 530 arranged and configured to engage at least a portion of the elongate member 301, such as through compression between respective radial outer surfaces of the drive wheel 520 and an idler wheel 530. At least one roller, such as the drive wheel 520, may be coupled to a manual drive wheel 510 via a transmission unit 540. The transmission unit 540 may include a gear set such as a spur gear, or one or more of chains, belts, or shaft couplings, among others. The manual drive wheel 510 may be coupled an axle securely attached to the base 550 or the housing 310 at a position such that a portion of the manual drive wheel 510 sticks outside the housing 310. A user may manually access and rotate the manual drive wheel 510 around the axle, which in turn drives rotation of the drive wheel 520, and frictionally move the elongate member 301 at a desired direction and speed.

In some examples, the manual motion control as in the external positioning unit 500 may be combined with the motorized motion control in the external positioning unit 300A or 300B. The drive wheel 520 and the idler wheel 530 may engage a first location of the elongate member 301 to manually control the implant motion, and the drive wheel 320 and the idler wheel 330 may engage a different second location of the elongate member 301 to robotically control the implant motion. In another example, a portion of the external positioning unit 500, such as the manual drive wheel 510 and the coupled transmission unit 520, may be incorporated into the external positioning unit 300A or 300B and coupled to the drive wheel 320. The drive wheel 320 may be subject to both a robotic control through the motor 342 and the power transmission unit 344, and a manual control through the manual drive wheel 510 and the coupled transmission unit 520. The robotic control and the manual control may be activated independently from each other. In an example, the user interface module 121 may enable a user to selectably enable a robotic mode for robotic motion control, or a manual mode for manual motion control of the elongate member 301. In an example, the manual mode may take priority over the robotic mode, such that a manual rotation of the manual drive wheel 510 may automatically override the robotic motion control. The manual override function may be utilized as a fail-safe emergency stop in case there is a fault in the motor 342 or the power transmission unit 344.

Figure 6A:
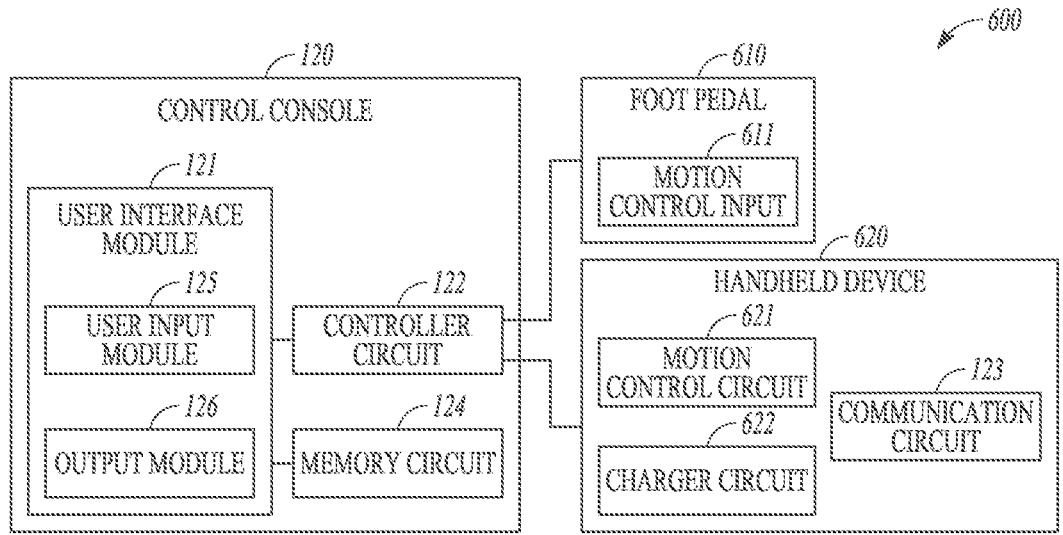
FIG. 6A illustrates, by way of example and not limitation, a block diagram of a portion of a control system for robotically assisted delivery and positioning of an implant.

FIG. 6A illustrates, by way of example and not limitation, a block diagram of a portion of a control system 600 for robotically assisted delivery and positioning of an implant. The control system 600 comprises a control console 120 coupled with one or more peripheral devices for implant motion control. The peripheral devices may include one or more of a foot petal 610, or a handheld device 620. In an event that the motor and the power system are included within the external positioning unit, the one or more peripheral devices may be communicatively coupled to the external positioning unit to directly control the motor output. The one or more peripheral devices may be communicatively coupled to the controller circuit 122 included in the control console 120, such as via a wired connection or a wireless communication link. Compared to the control console 120, the peripheral devices may have smaller size, lighter weight, and more mobility, thereby may provide enhanced operation flexibility. Some peripheral devices, such as a foot pedal, may be reusable. The materials need not be sterilizable or biocompatible to the level at which the external positioning unit materials do.

The foot pedal 610 may provide the surgeon with the means to control the motion of the implant. The foot pedal may be positioned under the patient table, accessible to the surgeon. The foot pedal 610 may comprise a motion control input 611. In an example, the motion control input 611 may include two or more pedals for use to control lead motion at different directions, such as one pedal to activate forward advancement motion, and another pedal to activate retraction motion to fine-tune the implant position or for implant extraction. In another example, the motion control input 611 may include two or more pedals for use to control lead motion at different lead orientation, such as one pedal to control the translational motion, and another pedal to control the rotational motion, as previously discussed with reference to FIG. 2. In yet another example, the motion control input 611 may include one pedal used for controlling implant advancement, and another pedal used for resetting the current implant position (i.e., setting the current position to zero). If a retraction action is needed, this may be an input on the control console 120, where the retraction command may be generated from the control console 120. This would prevent accidental retraction of the implant by stepping on the wrong pedal.

In some examples, each foot pedal may be incorporated with one or more command buttons or switches that are programmed for different functions, such as for controlling various motion parameters including motion rate, motion distance, or amount of force applied to the implant during insertion. In an example, different motion control actions may correspond to programmed duration when pedal is pressed and held, or patterns of the pedal press (such as one press, double press, or a combination of short and long press). For example, a short press may set the current implant position to zero (i.e., position reset), and a long press (e.g., press and hold for at least three seconds) may advance the implant. In an example, one press or button push may correspond to a specific distance of movement, such as 100 micron during a cochlear implantation procedure. In another example, the rate of insertion or the distance of the movement may vary based on a degree of foot pedal displacement up to the maximum set insertion rate and distance as programmed by a user via the user interface module 121.

The handheld device 620 may include a motion control input 621, such as buttons, switches, or other selection and activation mechanisms to control one or more motion parameters of the implant. In some examples, the communication circuit 123 may be implemented inside the handheld device 620. In an example, the communication circuit 123 may communicate with the external positioning unit 210 via a wireless communication link, including transmitting the motor control signal to the electric motor 231, and receive sensor feedback from one or more sensors located at the power system 230 or the external positioning unit 210. The mobility of the handheld device may allow for enhanced reliability of wireless communication. In some examples, the handheld device 620 may include a charger circuit 622 for wirelessly charging a power source for powering up the electric motor such as located inside the external positioning unit.

Figure 6B:
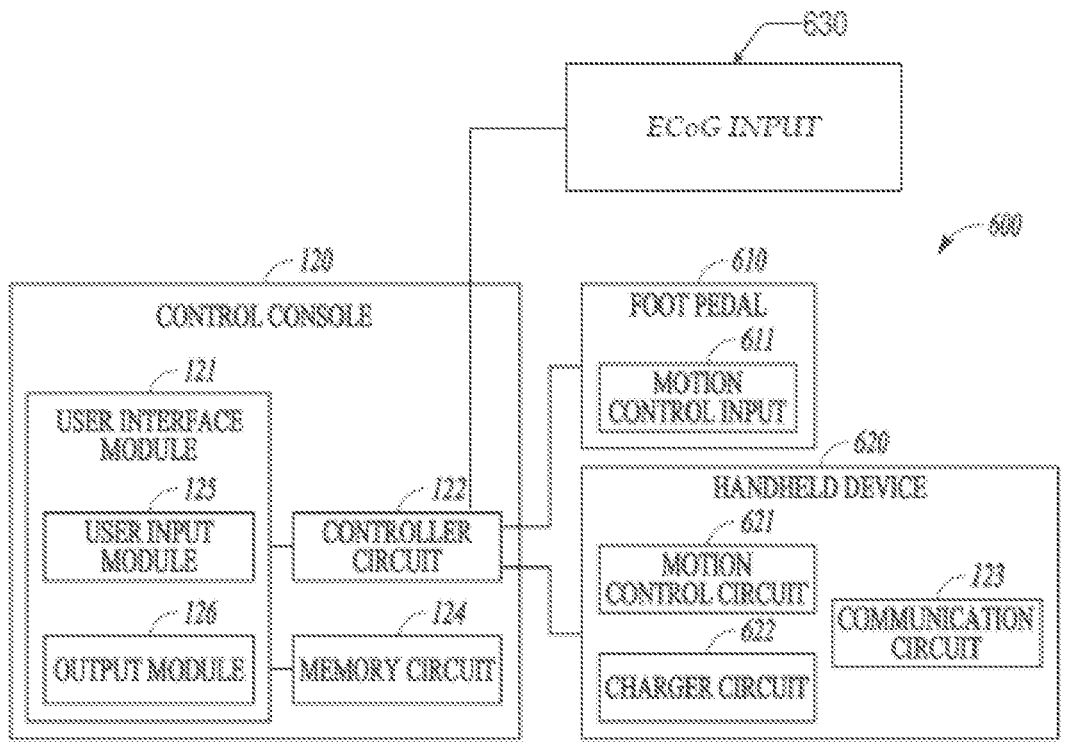
FIG. 6B illustrates, by way of example and not limitation, a block diagram of a portion of a control system for robotically controlling delivery and positioning of an implant using real-time feedback.

FIG. 6B illustrates, by way of example and not limitation, a block diagram of a portion of a control system for robotically controlling delivery and positioning of an implant using real-time feedback. In this example, the control system 600 can optionally include an ECoG input 630. The ECoG input 630 can supply ECoG measurement data in real-time to the controller circuit 122. The ECoG input 630 can link the control system 600 to ECoG measures, such as cochlear microphonics (CM), auditory nerve neurophonics (ANN), which can reflect immediate changes in the cochlear mechanics and insertion trauma pre-, during-, and post-insertion of the electrode array. This type of data can be utilized by the controller circuit 122 to control implant delivery and positioning in real-time with closed-loop feedback based on the ECoG measurements. ECoG recordings are electrical potentials generated in the inner ear, cochlea, and auditory nerve in response to sound or electrical stimulation, using an electrode placed at the sites such as the ear canal, tympanic membrane, round window, or intracochlear. While auditory brainstem responses (ABRs) reflect electrophysiological responses from different neural generators along the brainstem, cochlear microphnics (CM) reflect intracochlear physiology of outer and inner hair cells.

As illustrated in FIG. 6B, the control system 600 can link, couple, or interface the motion control parameters with real-time, intraoperative electrophysiological measures of cochlear function during electrode insertion to serve as means to determine and set optimal electrode positioning. Interoperability can include linking the software/data from the electrode array or other intracochlear/extracochlear recordings during real-time insertion to the control console feedback mechanism to indicate when optimal electrode position has been achieved based on electrophysiological measures such as neural response telemetry, auditory nerve neurophonics, or cochlear microphonics.

Decreased ECoGs during or after insertion likely reflect changes in cochlear mechanics due to the implant intracochlear position as well as insertion trauma, which are likely mechanisms of hearing loss after implant insertion. For example, CM amplitude changes have been shown to be most affected by inadvertent movement of the array upon physical contact/elevation of the basilar membrane. Therefore, the ability to provide a real-time monitoring link (via ECoG input 630) and feedback to the insertion control system 600 to monitor and fine tune the implant position by robotic-assisted and surgeon controlled micromechanical position adjustments until the ECoG measures such as CM are maintained or optimized per surgeon or audiologist determined preferences. In certain examples, the user interface module 121 can provide real-time feedback of the ECoG measures to the surgeon and enable additional controls responsive to ECoG measures and surgeon input.

With the real-time control system link and interface with ECoG measures during implant insertion, the system may notify the surgeon of potential for real-time physiological injury to intracochlear structures such as contact with the basilar membrane. If decreases or significant changes are recorded in ECoG measures, the system provides feedback to the surgeon in the form of visual or audible notifications and a stop command may be sent to the system controller to prevent further implant motion. After the system notification to the user, the surgeon may adjust implant insertion trajectory or system motion parameters as needed to avoid intracochlear damage or suboptimal electrode position or choose to the override notifications via physical acknowledgement mechanism. After acknowledgment of warning notification, the stop feedback is removed and the surgeon may continue robotic-assisted insertion of the implant.

Figure 7:
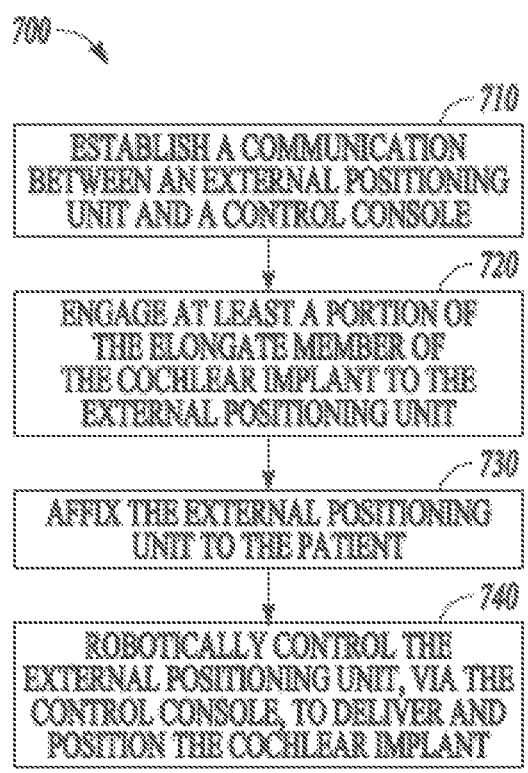
FIG. 7 illustrates, by way of example and not limitation, a method for delivering and positioning an implant into a target implantation site of a patient via an external, non-implantable robotically controlled implantation system.

FIG. 7 illustrates, by way of example and not limitation, a method 700 for delivering and positioning an implant into a target implantation site of a patient via an external, non-implantable robotically controlled implantation system, such as the robotically assisted implantation system 100. In an example, the method 700 may be used to operate the robotically controlled implantation system to advance an electrode array of a cochlear implant to a target cochlear region to restore hearing loss via electrostimulation. The method 700 may also be used for operating the robotically controlled implantation system to deliver, steer, position, or extract other types of implants or prosthesis. Examples of such implants may include leads, catheter, guidewire, or other mechanical or electrical devices. The implants may be used for diagnosing a disease or other conditions, or alternatively or additionally be used m the cure, mitigation, treatment, or prevention of disease, such as implantable electrodes for delivering electrostimulation at cardiac, neural, muscular, or other tissues.

The method 700 begins at step 710, where a communication link is established between an external positioning unit and a control console. The external positioning unit includes mechanical components for engaging a portion of an elongate member of the implant. The external positioning unit may also include a power system with a motor to generate driving force and motion, and a power transmission unit to transmit the driving force and motion from the motor to motion of the elongate member of the implant. The controller console include circuitry for generating a motion control signal according to the motion control instructions provided by the user. The motion control signal may control the power system to regulate one or more motion parameters of the elongate member.

The communication link between the external positioning unit and the control console may include a wired connection including universal serial bus (USB) connection, or otherwise cables coupled to communication interfaces on both the control console and the power system. In another example, the communication link may include a wireless connection including Bluetooth protocol, Bluetooth low energy protocol, near-field communication (NFC) protocol Ethernet, IEEE 802.11 wireless, an inductive telemetry link, or a radio-frequency telemetry link, among others.

At 720, at least a portion of the elongate member of a cochlear implant may be engaged to the external positioning unit. The cochlear implant may include an implantable stimulator for subcutaneous implantation under the scalp. The implantable stimulator may generate electrostimulation impulses conducted to the electrode array for stimulating cochlear nerves. The cochlear implant may include an elongate member with an electrode array disposed at a distal portion of the elongate member. The external positioning unit may include a coupling unit that may interface with the elongate member. In an example, the coupling unit may include a drive wheel and an idler wheel arrangement as illustrated in FIGS. 3A-3B. The elongate member of the implant may be fed through the external positioning unit via an entrance port and an exit port, and compression-engaged between the driver wheel and the idler wheel. The idler wheel may be spring-biased and compress against the driver wheel, via a torsion spring. The torsion spring may be manually biased to release the compression and open the space between the drive wheel and the idler wheel to accommodate the elongate member into the external positioning unit.

At 730, the external positioning unit may be affixed to a patient, such as on the patient head to maintain sufficient stability during the advancement of the implant. The external positioning unit may alternatively be securely attached to an object at the patient's immediate environment such as an equipment attached to a surgical table. As previously discussed with reference to FIG. 1, the external positioning unit may be sized and shaped to facilitate patient attachment. The external positioning unit may include a fixation member, such as one or more of a screw, a pin, a nail, a wire, a hook, a suture, or a magnet. The external positioning unit may have an exterior contact surface with a rough texture, or equipped with one or more gripping elements. Examples of the gripping elements may include penetrators such as spikes, pins, or barbs protruding from the exterior surface. When the exterior contact surface is in contact with a body part of the patient (e.g., patient head) and the external positioning unit is pressed and held against the body part, the gripping elements may provide sufficient friction or gripping force to securely hold the external positioning unit in place during the implant advancement.

At 740, an implant may be delivered and positioned into the target implantation site through a robotic control of the external positioning unit. In an example of cochlear implant, the electrode array of the cochlear implant may be inserted into and positioned at the target cochlear site. In patients with impaired high-frequency hearing function but preserved low-frequency hearing function, a short electrode array of the implant may be positioned at the outer or basal cochlea. Electrostimulation may be delivered therein via the electrode array to restore high-frequency hearing function. The robotic control of the implant movement may involve generating a motor control signal from the control console according to user programming instructions. The motor control signal may be transmitted to a motor located inside the control console or inside the external positioning unit. The motor may generate driving force and motion that control various motion parameters of the elongate member of the implant via the power transmission unit. The control console may regulate the electrode array movement further based on sensor feedback on the position of the implant, motion the implant, or the force or friction applied to the implant. Examples of the robotically assisted delivery and positioning of the implant are discussed below, such as with reference to FIG. 8.

Figure 8:
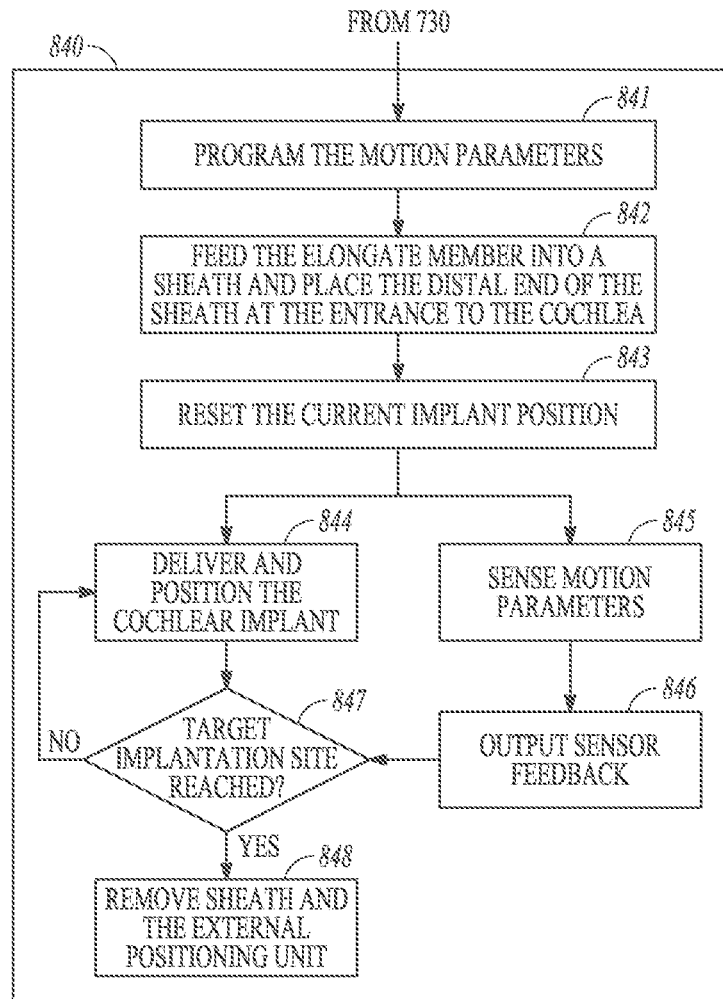
FIG. 8 illustrates, by way of example and not limitation, a method for sensor-based robotic control of a cochlear implant.

FIG. 8 illustrates, by way of example and not limitation, a method 840 for sensor-based robotic control of a cochlear implant. The method 840 is an embodiment of the step 740 of the method 700 as illustrated in FIG. 7. The method 840 may be used for operating a non-implantable, robotically controlled implantation system, such as the robotically assisted implantation system 100.

Once the external positioning unit is affixed to the patient at 730, motion control parameters may be programmed at 841, such as via the user interface module 121 of the control console 120. The motion control parameters may characterize desired motion of the elongate member of the implant. Examples of the motion parameters may include a target movement rate, a target movement direction or orientation, a target movement distance, a target position of a distal end of the elongate member, or a target amount of force imposed on the elongate member. In some examples, a pre-determined implant delivery protocol may be programmed into the system. The implant delivery protocol defines target values of a plurality of motion parameters. A user may adjust one or more motion parameters, modify an existing implant delivery protocol, or switch to a different implant delivery protocol during the implant delivery procedure.

At 842, the elongate member of the implant may be fed into a sheath, and a distal end of the sheath may be introduced to the entrance of the surgical site, such as a cochlear entrance for cochlear implant placement. As illustrated in FIGS. 3-4, the sheath may partially or completely enclose the elongate member of the implant to provide resilient support to the elongate member, thereby keeping the implant on track from the external positioning unit and the surgical entrance of the target implantation site. A surgeon may advance the implant through the external positioning unit via user input controls on the user interface module, or through a peripheral input device such as a foot pedal or a handheld device, until the distal tip of the elongate member is in line with distal end of the sheath. The distal end of the sheath may then be positioned at the entrance to the cochlea. The distal end of the sheath may be fixed or reversibly stabilized at a designated position of the surgical opening of the implantation. In an example of cochlear implant, the distal end of the sheath may be stabilized at the cochlea round window (RW) or cochleostomy site by closely matching tube diameters to the RW niche or cochleostomy dimensions.

Once the sheath are positioned and stabilized in place, the implant may be robotically advanced via the control console or one or more of the peripheral input controls coupled to the control console. At 843, the current implant position may be reset to zero, such as by a short press of the foot pedal. At 844, the cochlear implant may be delivered and positioned to the target site of cochlear region, according to the programmed motion control parameters. The motion of the implant may be activated by a surgeon using the control buttons on the control console, or a peripheral control device, such as a foot pedal or a handheld device. The movement of the implant may be activated at intervals of a predetermined step size. In an example, for cochlear implant, the target movement rate is approximately 100 micron intervals. In an example, the target movement distance is approximately 1-35 millimeters.

During the implantation process, one or more sensors may sense information about position and motion of the implant at 845. The sensor may be positioned at the electric motor, the power transmission unit, or inside the external positioning unit such as at the drive wheel or idler wheel. Examples of the sensors may include encoders. Hall effect sensors, or optional sensors for detecting the position of the implant, capacitive sensors for detecting implant motion, or force sensors for sensing a parameter indicative of force or friction imposed on the implant during the implant advancement, such as axial, lateral, or radial insertion force as the implant advances into the cochlea. The force may also be indirectly sensed by measuring the current supplied to the electric motor.

At 846, the sensor feedback on implant may be transmitted to the control console and output to a user or a process. In an example, a human-perceptible presentation of the sensed feedback, including one or more parameters on the position of the implant, motion of the implant, or the force or friction applied to the implant motion, may be generated. The presentation may include real-time visual or audible notification with specified patterns corresponding to different types of events encountered during implantation. The audible and visual feedback may also signal to the user that the sensed implant position, motion, or the forces has exceed the target parameter values such as programmed by the user.

At 847, the sensor feedback is checked to determine whether target implantation site has been reached. A target implantation site is reached if the sensed distance of insertion reaches the user programmed target distance within a specified margin. A visual indicator, such as a light emitting diode (LED) or an on-screen visual indicator on the display screen with specified color or pattern may signal to the user a successful positioning of the implant at the target implantation site. Alternatively or additionally, an audial notification, such as a beep or an alarm with a specific tone, frequency, or a specific pattern (e.g., continuous, intermittent, pulsed, sweep-up, or sweep-down sound) may go off to signal to the user successful positioning of the implant at the target implantation site.

If at 847 the target implantation site is not reached, then the delivery and positioning process may be continued at 844. If at 847 it is determined that the target implantation site has been reached, then at 848, the implant may be released and positioned at the target implant site, and the sheath and the external positioning unit may be removed. As illustrated in FIGS. 4A-4C, the sheath may include disengagement means to facilitate separation of the sheath from the elongate member, while at the same time avoid excessive damaging forces on the implant, such as to prevent dislodgement of the implant from the implantation site upon removal of the sheath.

Figure 9:
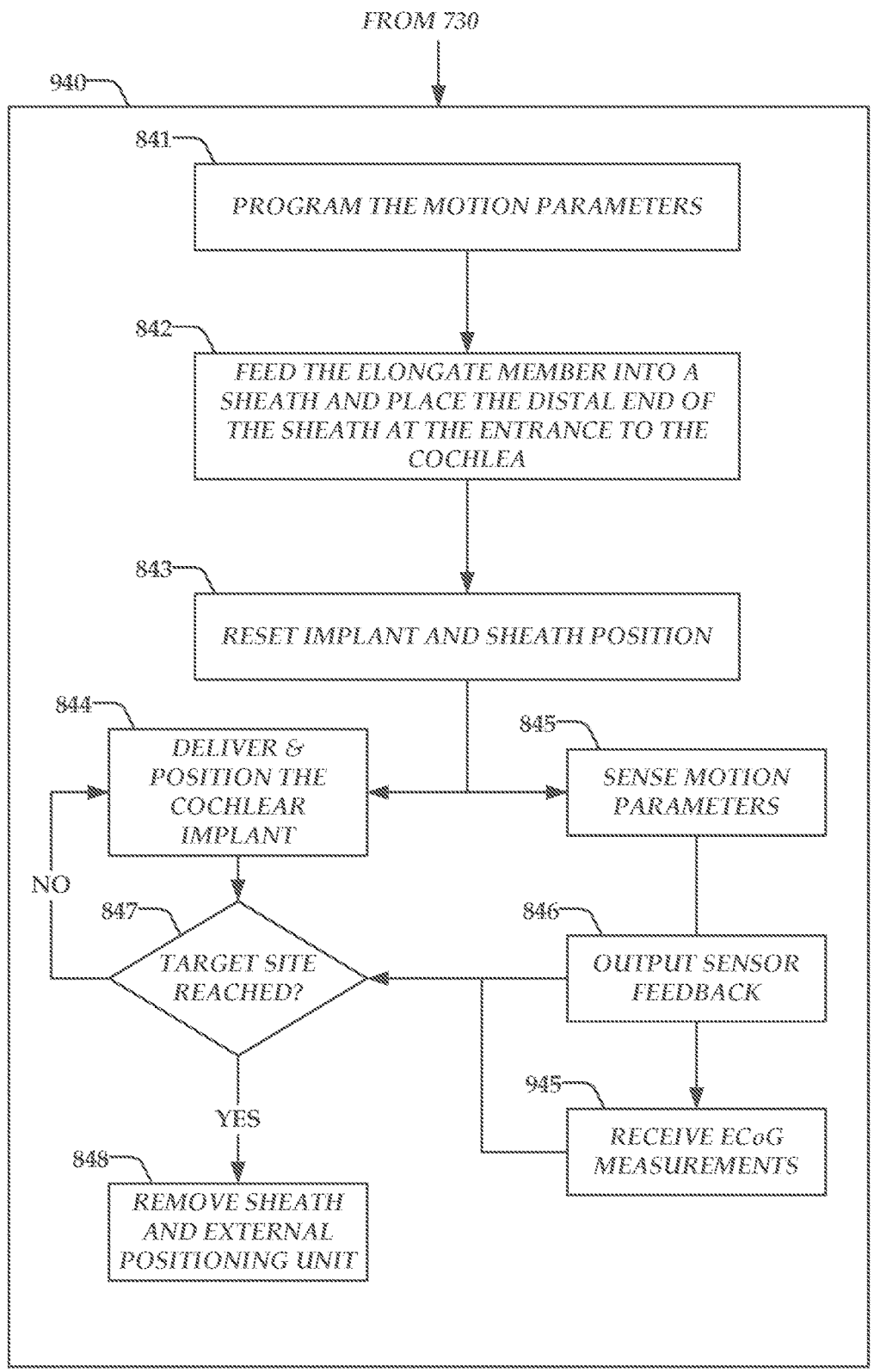
FIG. 9 illustrates, by way of example and not limitation, a method for sensor-based and measurement-based real-time control of implant delivery and positioning.

FIG. 9 illustrates, by way of example and not limitation, a method for sensor-based and measurement-based real-time control of implant delivery and positioning. The method 940, like method 840 discussed above, is an embodiment of the step 740 of the method 700 as illustrated in FIG. 7. The method 940 may be used for operating a non-implantable, robotically controlled implantation system, such as the robotically assisted implantation system 100. In this example, the method 940 includes operations identical to method 800 with the addition of receiving ECoG measurements at 945. As discussed in reference to FIG. 6B above, the ECoG measurements can be utilized by the external positioning unit 110 and/or control console 120 to assist in controlling implant positioning and delivery. As illustrated in FIG. 9, the method 940 can include an operation for receiving ECoG measurements, which can then be utilized in determining whether a target site is reached at 847. As discussed above, ECoG measurements can be monitored to determine when an optimal implant position is reached or for potential issues with the implant delivery.

Figure 10A:
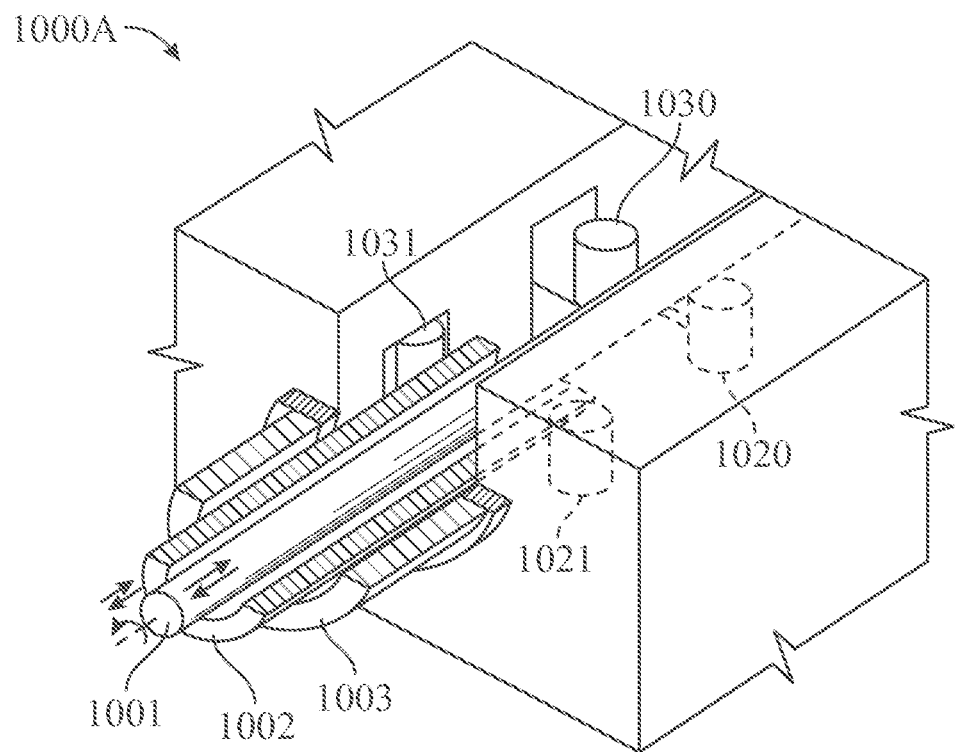
FIGS. 10A-10B illustrate, by way of example and not limitation, a portion of an external positioning unit configured to deliver and position a guide sheath and an implantable electrode.
Figure 10B:
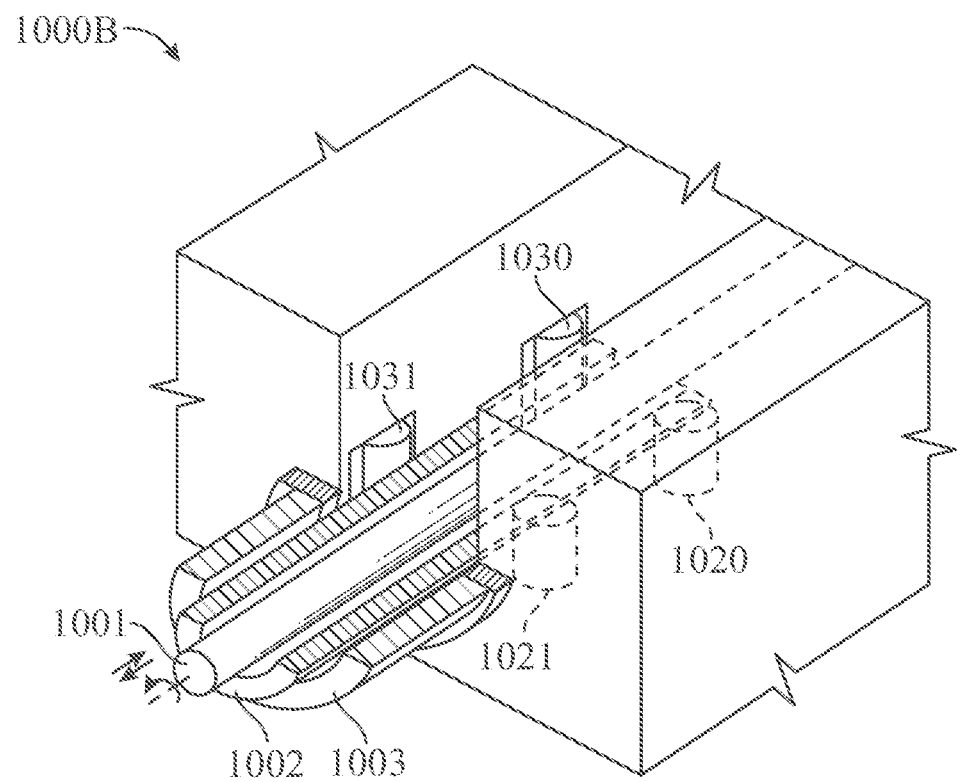

FIGS. 10A-10B illustrate, by way of example and not limitation, a portion of an external positioning unit configured to deliver and position a guide sheath and an implantable electrode. Similar to FIGS. 4A-4C, these figures expound on the example external positioning devices illustrated in FIGS. 3A-3B. External positioning units 1000A and 1000B illustrate alterations to the external positioning units discussed above to handle positioning of both an electrode (elongate implant) as well as a guide sheath, such as insertion sheath 1002 (also referenced as an internal sheath). Similar to the systems discussed above, the external positioning units 1000A/1000B include a guide sheath 1003 that can be fixed to the external positioning unit. Within the guide sheath 1003 is an insertion sheath 1002 and an electrode implant 1001. The other addition illustrated in FIGS. 10A-10B are another set of drive and guide wheels (see spring loaded sheath wheel 1031 and sheath drive wheel 1021 as well as spring-loaded electrode wheel 1030 and drive wheel 1020.

As mentioned above, intracochlear trauma can occur from large pressure spikes generated during the insertion of cochlear implant electrodes. Similar fluid and force spikes can be elicited from any solid or flexible bodies, tubes, or sheaths inserted into the cochlea. These pressures spikes may be of sufficient intensity to cause trauma similar to that of an acoustic blast injury and are one likely source for postoperative loss of residual hearing.

Similar to the insertion trauma cause by electrode insertion, the manual insertion of a sheath or other solid body/tube manually into the cochlea may cause intracochlear fluid pressure spikes and result in intrachochlear damage. To help preserve residual hearing and prevent these traumatic events from manual, un-assisted implantations, external positioning unit 1000A/1000B includes an additional method to perform guide sheath or insertion sheath insertion near or into the cochlea utilizing the robotic-assisted stage and control console system. The system's micro-mechanical movements and control of both the implant, guide sheath or insertion sheath serves to reduce the magnitude and frequency of both insertion pressure and insertion forces during cochlear implantation.

In this example, the guide sheath 1003 supports and internally houses an insertion sheath/tube 1002 in a telescoping fashion. The insertion sheath 1002 can slide within the guide sheath 1003 and over the electrode implant 1001 also housed within. The insertion sheath 1002 moves through the guide sheath 1003 (affixed to the external positioning unit proximally) and over the implant 1001 on the abluminal side within. This enables controlled robotic movement of both the insertion sheath 1002 and implant 1001 into the delicate intracochlear space.

The system may be capable of parallel telescoping or rotational movements of both insertion sheaths and implant within a guide sheath in a coordinated, surgeon controlled fashion utilizing two or more coupling units within the external positioning unit. There may either be two independent drive wheel coupling systems each controlling the sheath and electrode insertion independently or in parallel, coordinated motions. After the end of the internal insertion sheath is inserted a distance that passes the distal coupling unit and travels out of the compressive grasp, the spring-loaded wheel will disengage from the internal insertion sheath and clamp onto the internal electrode implant. The now directly interface implant is then controlled robotically with the same drive wheel control unit via user controlled motion parameters.

FIG. 10A illustrates the insertion sheath 1002 engaged with spring-loaded sheath wheel 1031 and sheath drive wheel 1021, which are controlling positioning of the insertion sheath 1002. The electrode implant 1001 is engaged by spring-loaded electrode wheel 1030 and electrode drive wheel 1020. In this example, the insertion sheath 1002 may be fully positioned, as the external positioning unit 1000A is engaged with the electrode implant.

FIG. 10B illustrates the insertion sheath 1002 engaged with both drive mechanisms within the external positioning unit 1000B. In this example, the spring-loaded sheath wheel 1031 and sheath drive wheel 1021 as well as the spring-loaded electrode wheel 1030 and electrode drive wheel 1020 are engaged with the insertion sheath 1002. In this example, the insertion sheath 1002 is still in the process of being positioned/delivered.

In these examples, systems for cochlear implant insertion are described, but the method and systems can apply to any thin cylinder, tubular or elongate member such as a sheath, neurostimulators, electrodes, or catheters insertion into any body tissue, cavity, or fluid filled space.

Figure 11:
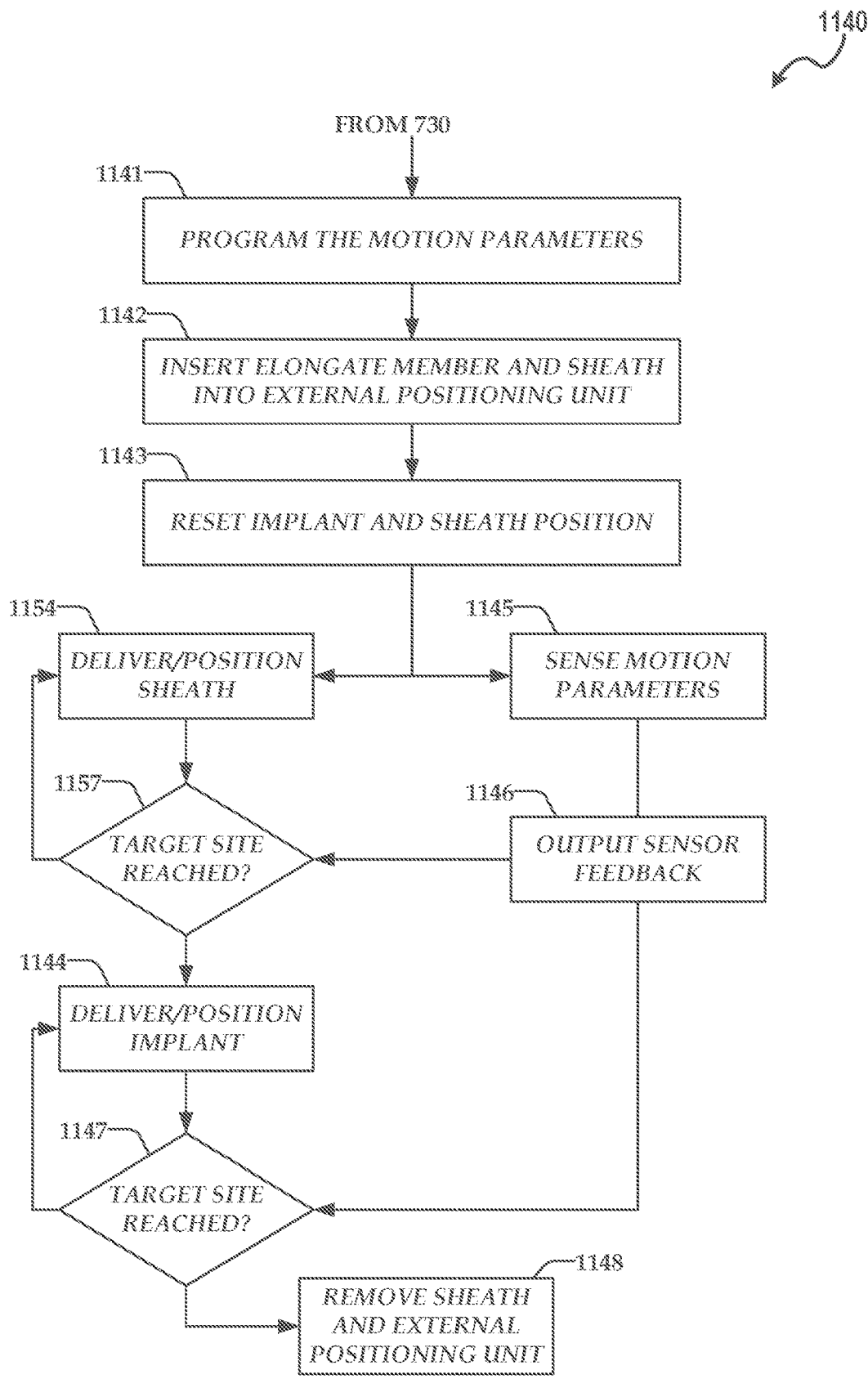
FIG. 11 illustrates, by way of example and not limitation, a method for real-time control of implant and guide sheath delivery and positioning.

FIG. 11 illustrates, by way of example and not limitation, a method for real-time control of implant and guide sheath delivery and positioning. The method 1140, like methods 840 and 940 discussed above, is an embodiment of the step 740 of the method 700 as illustrated in FIG. 7. The method 1140 may be used for operating a non-implantable, robotically controlled implantation system, such as the robotically assisted implantation system 100. In this example, the method 1140 includes operations identical to method 840 with the addition of operations for monitoring the positioning and delivery of an insertion sheath, such as insertion sheath 1002. As illustrated, the method 1140 includes additional operations 1154 and 1157 for delivering and/or positioning a sheath at 1154 and determining whether the sheath has reached the target position at 1157. Monitoring the sheath insertion can involve similar sensor feedback as used with electrode insertion. Otherwise, the operations of method 1140 mirror those discussed in reference to methods 840 and 940 above.

Figure 12A:
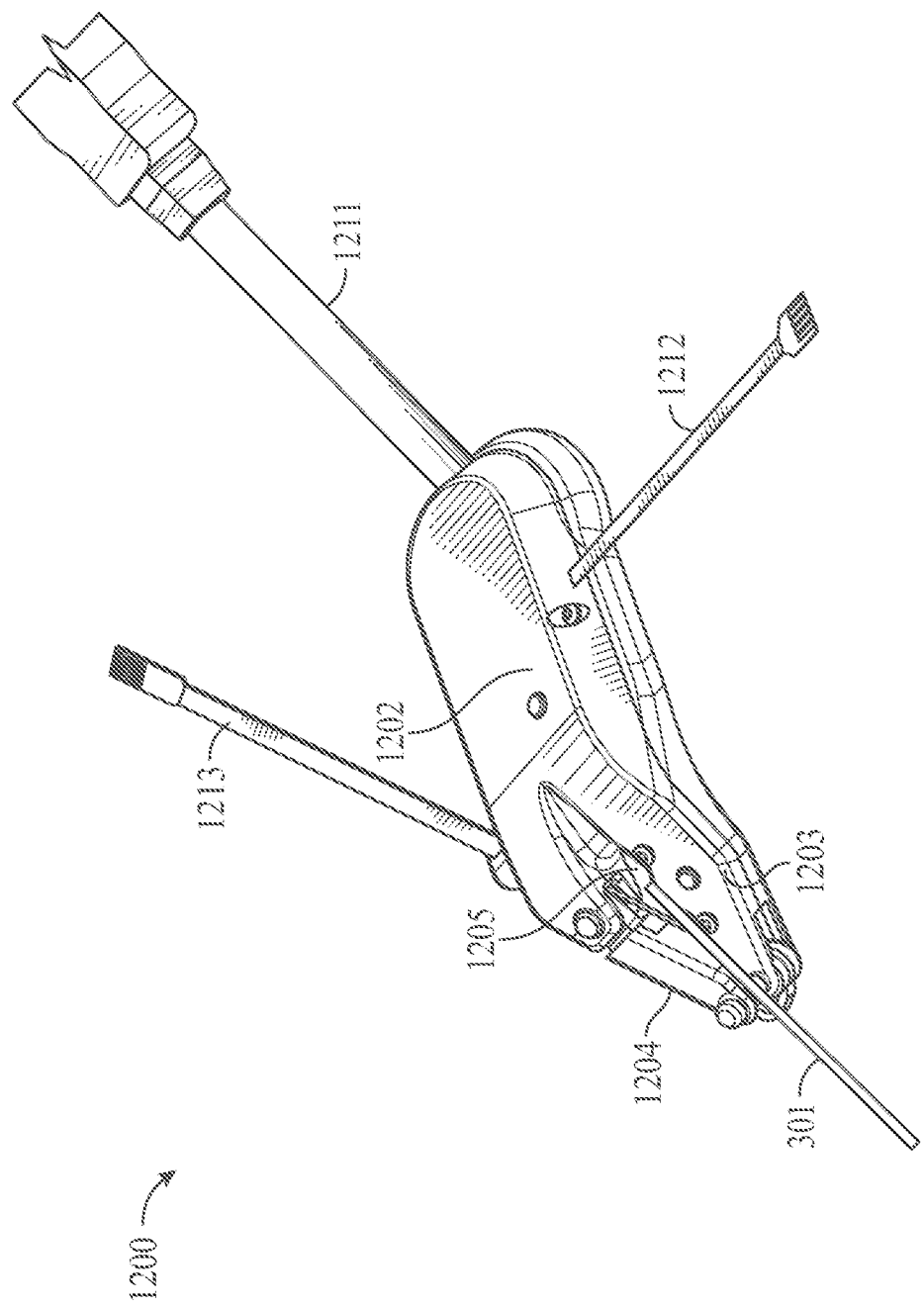
FIGS. 12A-12C illustrate, by way of example and not limitation, diagrams of different views of a portion of an external positioning unit.
Figure 12B:
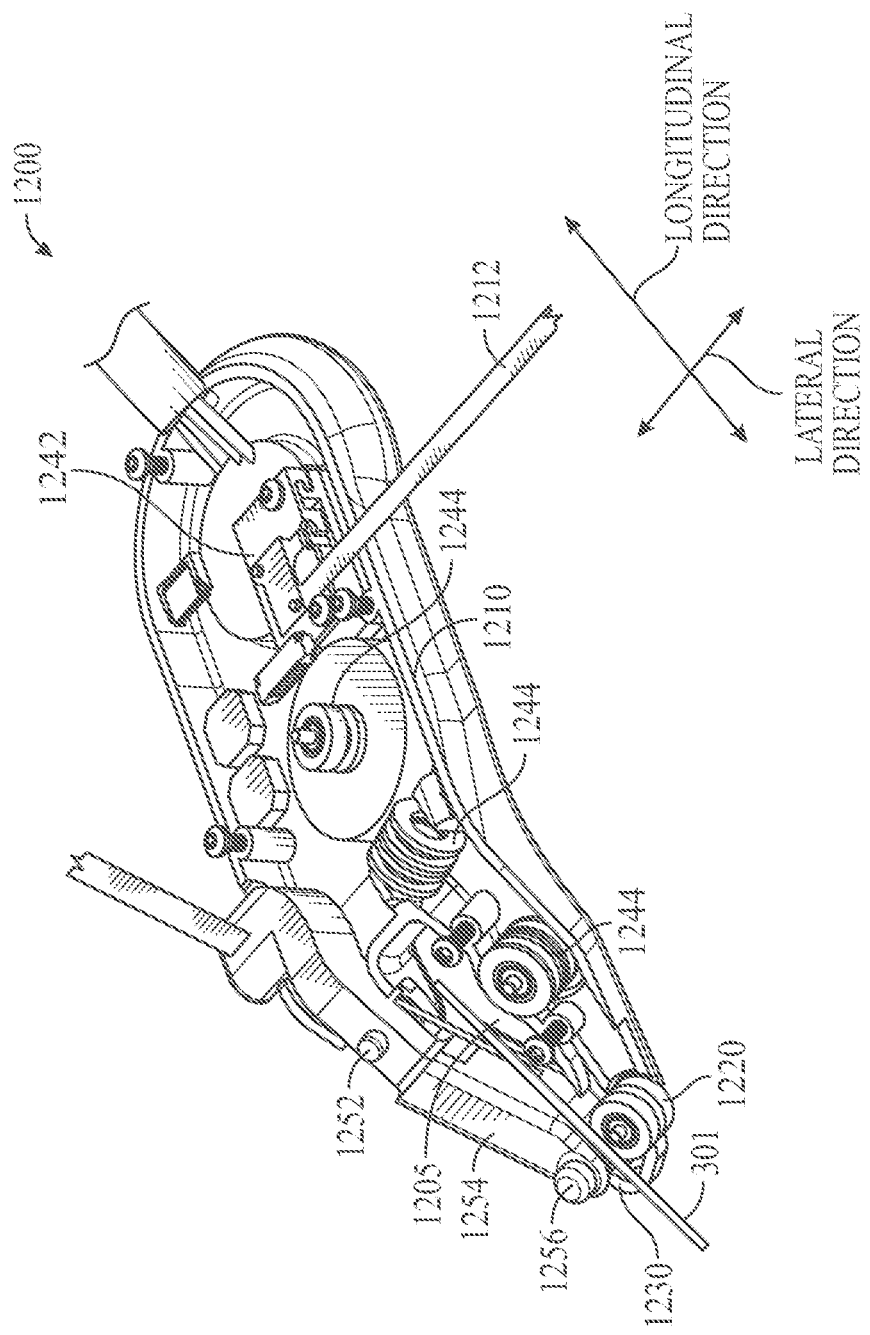
Figure 12C:
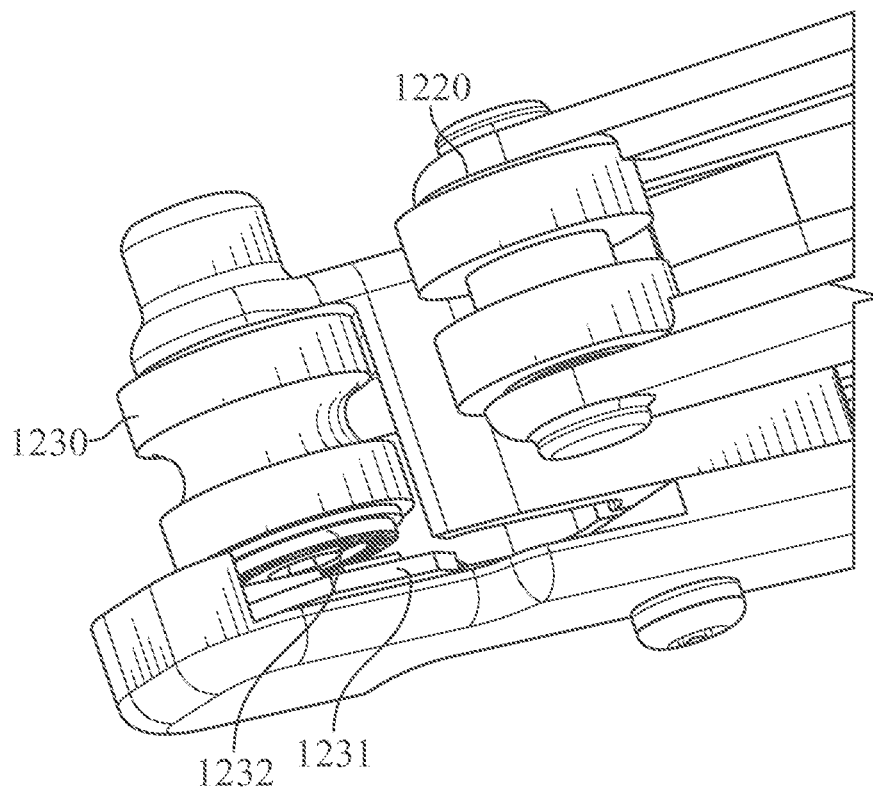

FIGS. 12A-12C illustrate, by way of example and not limitation, diagrams of different views of a portion of an external positioning unit 1200, which represents an embodiment of the external positioning unit 110 as illustrated in FIG. 1. FIG. 12A is a perspective diagram of the external positioning unit 1200. The external positioning unit 1200 includes a unit body 1202, and first and second arms 1203 and 1204 extending from the unit body 1202. The unit body 1202 and the first and second arms 1203 and 1204 house an assembly of electro-mechanical components interconnected to engage an elongate member 301 and robotically deliver and position the implant attached to the elongate member 301 into a target implantation site. The external positioning unit 1200 includes a power or charging cable 1211, and one or more of control and communication cables 1212 and 1213 to receive signals to control the motor output and thus the motion of the implant. In an example, the external positioning unit 1200 may include a battery as power source. The battery may be a rechargeable battery. The first and second arms 1203 and 1204 may each house respective coupling units at their distal ends that are in movable contact with each other, such as the coupling unit 111 and 211 as discussed above with reference to FIGS. 1-2.

As illustrated in FIG. 12A, the first and second arms 1203 and 1204 may each be tilted at an angle with respect to the plane of the unit body 1202, and operably form an open space 1205 to accommodate at least a portion of the elongate member 301. In various examples, the first and second arms 1203 and 1204 may be multiple degrees of freedom of tilt to different axes. The tilted arms and the open space in between may also allow the elongate member 301 to move longitudinally without being interfered by the unit body 1202.

FIG. 12B is a cutaway view of the external positioning unit 1200 that illustrates an electro-mechanical assembly enclosed by a housing 1210. The unit body 1202 houses an electric motor 1242 that may generate driving force and motion according to a motion control signal, such as provided by the control console 120 and transmitted through the control and communication cable 1212. The electric motor 1242 is coupled to a power transmission unit 1244, which represents an embodiment of the power transmission unit 232 as illustrated in FIG. 2. By way of example and not limitation, the power transmission unit 1244 may include a series of pulleys connected by belts (not shown). Rotation of the pulleys may transmit the power to a drive wheel 1220 enclosed in the first arm 1203. Similar to the drive wheel 320 in FIG. 3A, the drive wheel 1220 may rotate on an axle securely attached to the housing 1210.

Enclosed in the second arm 1204 may include an idler wheel 1230, which is an embodiment of the idler wheel 320 in FIG. 3A. The idler wheel 1230 may be coupled to a biasing system that includes a spring-loaded lever 1254 coupled to a torsion spring 1252. The second arm 1204 may additionally house a sensor to sense motion parameters. FIG. 12C illustrates an embodiment of such a sensor. An encoder sensor 1231 may sense the rotation of the idler wheel 1230 (thus the motion parameters of the elongate member 301) via an encoder wheel 1232 attached to the idler wheel 1230. Examples of the encoder sensor 1231 may include optical, capacitive, or Hall effect based sensors. The spring-loaded lever 1254, through a spring bias 1256, may support the idler wheel 1230, and provide lateral compression against the drive wheel 1220. The tension generated by the torsion spring 1252 may be relayed to the idler wheel 1230 via the spring-loaded lever 1254, and compress against the drive wheel 1220 to generate adequate friction on the elongate member 301. Depending on the motion control signal input to the motor 1242, the power transmission unit 1244 may drive rotation of the drive wheel 1220, which in turn propels the implant to a specific direction (e.g., forward or backward) at a specific rate. As illustrated in FIG. 12B, the torsion spring 1252 may be coupled to a button 1252 that allows a user to control the spring tension. For example, a user may push the button 1252 to release the compression and open the idler wheel 1230 away from the drive wheel 320. In some examples, the release of the compression may allow a user to easily move the second arm 1204 away from the first arm 1203. The user may then remove the elongate member 301, or load another implant with an elongate member into the external positioning units 1200. Because the idler wheel 1230 is held in place by the biasing system, the idler wheel 1230 may move laterally relative to the housing 1210, thus may accommodate elongate members with various diameters or cross-sectional shapes, while maintaining sufficient friction on the elongate member for desirable movement.

Figure 13A:
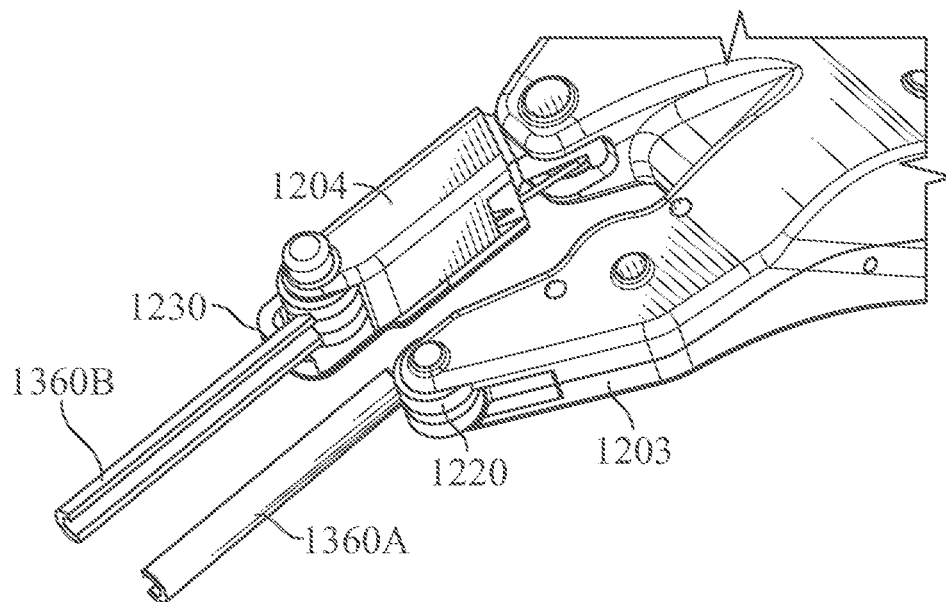
FIGS. 13A-13B illustrate, by way of example and not limitation, diagrams a portion of an external positioning unit coupled with a guide sheath.
Figure 13B:
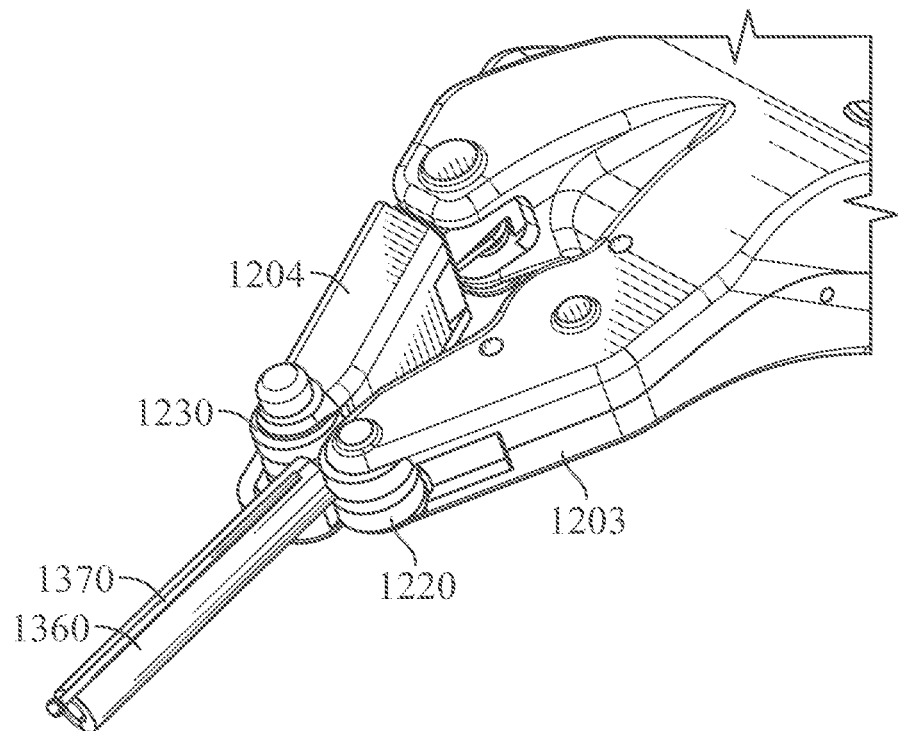

FIGS. 13A-13B illustrates, by way of example and not limitation, diagrams a portion of the external positioning unit 1200 coupled to a removable guide sheath 1360. The guide sheath 1360 represents an embodiment of the sheath 360 or one of 460A-460C. In the illustrated example, the guide sheath 1360 comprises two separable portions 1360A and 1360B removably affixed to the first and second arms 1203 and 1204, respectively. FIG. 13A illustrates the sheath portions 1360A and 1360B in open position. When the second arm 1204 is moved away from the first arm 1203 such as via the spring mechanism in the spring-loaded lever 1254, the sheath portion 1360B, affixed to the second arm 1204, may be separated and moved away from the sheath portion 1360A. FIG. 13B illustrates the sheath portions 1360A and 1360B in closed position, which can be achieved by moving the second arm 1204 towards the first arm 1203. The closed position may be maintained by the compression provided by the spring-loaded lever 1254. The closure of the sheath portions 1360A and 1360B may at least partially enclose the elongate member 301 to provide resilient support to the elongate member 301 of the implant, prevent buckling in the implant from the controlled force of the insertion device, and keep the implant on track during guided implant delivery, such as insertion into the implant site. Once the implant is fully inserted, the guide sheath 1360 may be safely removed, such as torn apart through linear perforations. In an example of cochlear implant, the guide sheath 1360A-1360B is flexible to direct distal end to the round window or cochleostomy insertion site.

In some examples, as illustrated in FIG. 15B, a sensing probe 1370 may be attached to the guide sheath 1360 to measure a physiologic signal, such as electrocochleography (EcoG) during cochlea implantation. In an example, the sensing probe 1370 may include an electrically conductive wire encompassed in the sheath material or via a separate sheath channel. By way of example and not limitation, the conductive wire may be made out of platinum, palladium, iridium, gold, or alloys. The wire has an exposed distal electrode that makes direct contact with the bone at the round window niche via a ball tip or wire loop end. This sensing electrode or probe interfaces at its proximal end with the main insertion system unit processor as an integrated sensing electrode. The EcoG measures obtained via the sensing electrode tip at the round window may be used as a physiologic feedback to optimize the insertion system control and positioning of the cochlear implant electrode.

Figure 14:
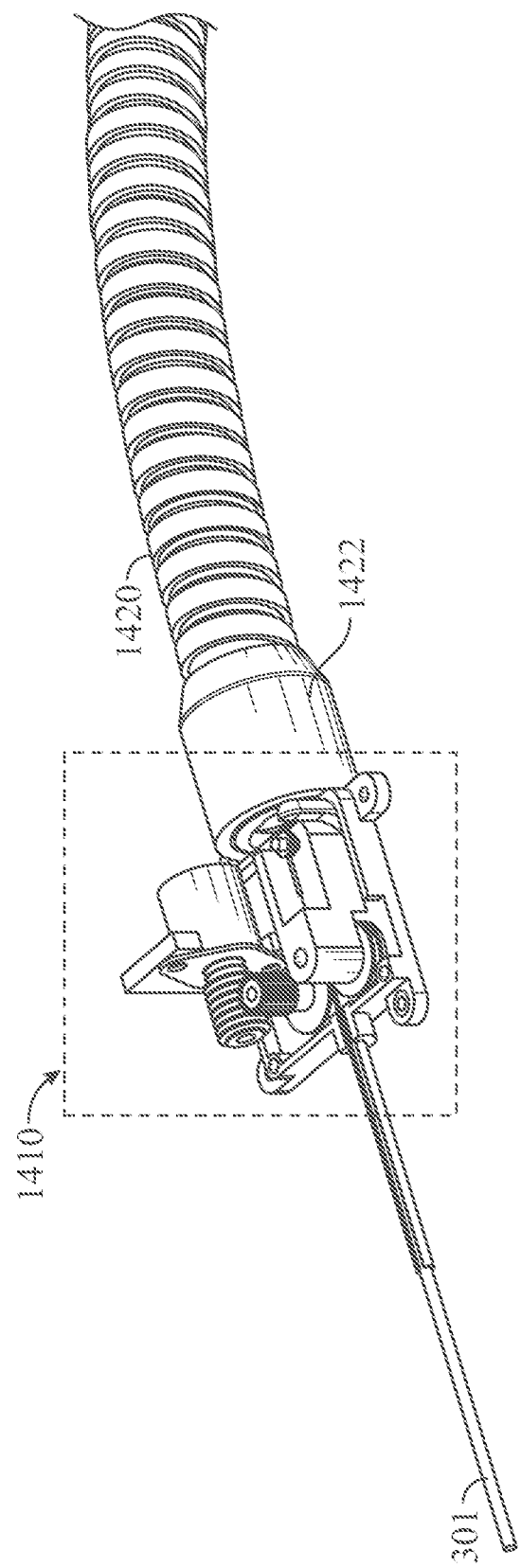
FIG. 14 illustrates, by way of example and not limitation, a diagram of an external positioning unit mounted on an adjustable arm.

FIG. 14 illustrates, by way of example and not limitation, a diagram of an external positioning unit 1410 mounted on an adjustable arm 1420. The adjustable arm 1420 can be a hollow, flexible, malleable arm such as a gooseneck tubing, as illustrated in FIG. 14. The adjustable arm 1420 is configured to allow the user to position the trajectory prior to insertion of the elongate member 301. The external positioning unit 1410 represents an embodiment of one of the external positioning unit 300A, 300B, 500, or a variation thereof, and can be attached to a distal end 1422 of the adjustable arm 1420 via detachable couplings. The gooseneck tubing is flexible, yet rigid and adjustable to hold the external positioning unit 1410 at user manually-set positions in space relative to the patient. In an example, one or more of the first and second arms 1203 and 1204 of the external positioning unit 1200 may take the form of the gooseneck tubing as illustrated in FIG. 14. The gooseneck tubing may support and hold in position the distal coupling units (e.g., the drive wheel 1220 and the idler wheel 1230), and acts as conduit for internal cables. In various examples, at least a portion of the motor 1242, the power transmission unit 1244, and drive cable (such as rotating shaft 356) may be housed within the hollow space of the flexible gooseneck tubing that snakes down to the coupling units at the distal end. This would provide surgeon flexibility to mechanically adjust the trajectory of insertion of the elongate member 301.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for use in implanting or manipulating an implant in a patient, the system comprising:
   a positioning unit, including:
      two rollers arranged to engage, through compression between respective radial outer surfaces of the two rollers, at least a portion of an elongate member of the implant;
      a manual actuator coupled to at least one of the two rollers and configured to receive driving force from a user to drive rotation of the at least one of the two rollers, said rotation actuating a translational motion or a rotational motion of the elongate member via friction generated by the compression between the two rollers; and one or more sensors, coupled to or included in the positioning unit, that are configured to sense a motion of the implant.

2. The system of claim 1, wherein the manual actuator is coupled to the at least one of the two rollers via a transmission unit.

3. The system of claim 2, wherein the transmission unit includes a gear or a gear set.

4. The system of claim 2, wherein the transmission unit includes an axle coaxially extending between the manual actuator and the at least one of the two rollers.

5. The system of claim 1, wherein the manual actuator includes a manual drive-wheel.

6. The system of claim 1, wherein the manual actuator is configured to disengageably engage with an insertion device operable by the user, and to receive the driving force from the user via the insertion device.

7. The system of claim 1, wherein at least one of the two rollers is spring loaded to provide the compression between the respective radial outer surfaces of the two rollers and to engage at least a portion of the elongate member.

8. The system of claim 1, further comprising a sheath extending from the positioning unit to a surgical entrance of an body site, the sheath configured to at least partially enclose the elongate member to provide resilient support thereto and to guide implant orientation or removal.

9. The system of claim 8, wherein the sheath includes a partially enclosed and partially open longitudinal track to support the elongate member.

10. The system of claim 8, wherein the sheath includes a first longitudinal track portion and a second longitudinal track portion running in parallel to the first longitudinal track portion, the first and second longitudinal track portions detachably attached to each other to enclose the elongate member.

11. The system of claim 8, wherein the sheath includes a disengaging member operable by the user to transmit a pulling stress to the sheath to cause detachment from the elongate member, the disengaging member including one or more release tabs attached to a circumferential surface of the elongate member.

12. The system of claim 11, wherein the sheath includes linear perforations thereon configured to tear and split the sheath in response to the pulling stress.

13. An apparatus for use in implanting or manipulating an implant in a patient, the apparatus comprising a positioning unit that includes:
two rollers arranged to engage, through compression between respective radial outer surfaces of the two rollers, at least a portion of an elongate member of the implant; and
a manual actuator coupled to at least one of the two rollers and configured to receive driving force from a user to drive rotation of the at least one of the two rollers, said rotation actuating a translational motion or a rotational motion of the elongate member via friction generated by the compression between the two rollers.

14. The apparatus of claim 13, wherein the manual actuator is coupled to the at least one of the two rollers via a gear or a gear set.

15. The apparatus of claim 13, comprising an axle coaxially extending between the manual actuator and the at least one of the two rollers.

16. The apparatus of claim 13, wherein the manual actuator includes a manual drive-wheel.

17. The apparatus of claim 13, wherein the manual actuator is configured to disengageably engage with an insertion device operable by the user, and to receive the driving force from the user via the insertion device.

18. The apparatus of claim 13, wherein the manual actuator is configured to drive rotation of the at least one of the two roller to actuate the translational motion or the rotational motion of the elongate member that propels the implant to a body site.

19. The apparatus of claim 13, wherein at least one of the two rollers is spring loaded to provide the compression between the respective radial outer surfaces of the two rollers and to engage at least a portion of the elongate member.

20. The apparatus of claim 13, further comprising a sheath extending from the positioning unit to a surgical entrance of a body site, the sheath configured to at least partially enclose the elongate member to provide resilient support thereto and to guide implant orientation or removal.

21. The apparatus of claim 20, wherein the sheath includes a partially enclosed and partially open longitudinal track to support the elongate member.

22. The apparatus of claim 20, wherein the sheath includes a first longitudinal track portion and a second longitudinal track portion running in parallel to the first longitudinal track portion, the first and second longitudinal track portions detachably attached to each other to enclose the elongate member.

23. The apparatus of claim 20, wherein the sheath includes a disengaging member operable by the user to transmit a pulling stress to the sheath to cause detachment from the elongate member.

24. A method for operating a positioning unit to implant or manipulate an implant in a patient, the method comprising:
engaging at least a portion of an elongate member of the implant through compression between respective radial outer surfaces of two rollers arranged in the positioning unit;
implanting, or affixing externally, the positioning unit to the patient; and
applying a manual driving force to a manual actuator to drive rotation of at least one of the two rollers against another of the two rollers, said rotation actuating a translational motion or a rotational motion of the elongate member via friction generated by the compression between the two rollers.

25. The method of claim 24, further comprising:
providing a sheath extending from the positioning unit to a surgical entrance of a body site; and
at least partially enclosing the elongate member longitudinally with the sheath to provide resilient support of the elongate member and to guide implant orientation or removal.

26. The method of claim 25, wherein at least partially enclosing the elongate member includes disposing at least a portion of the elongate member in a partially enclosed and partially open longitudinal track included in the sheath.

27. The method of claim 25, wherein at least partially enclosing the elongate member includes enclosing the elongate member with a first longitudinal track portion and a second longitudinal track portion detachably attached to, and running in parallel to, the first longitudinal track portion.

28. The method of claim 27, further comprising disengaging the first longitudinal track portion from the second longitudinal track portion at a conclusion of the implantation.

29. The method of claim 25, wherein at least partially enclosing the elongate member includes inserting at least a portion of the elongate member into the sheath, the sheath having a disengaging member attached thereto.

30. The method of claim 29, further comprising applying a pulling stress to the disengaging member to detach the sheath from the elongate member at a conclusion of the implantation.

* * * * *